(12) United States Patent
Liras et al.

(10) Patent No.: US 6,444,679 B1
(45) Date of Patent: Sep. 3, 2002

(54) 4-PHENYL-4-HETEROARYLPIPERIDINE DERIVATIVES

(75) Inventors: Spiros Liras, Stonington, CT (US); Stanton F. McHardy, Coventry, RI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/503,679

(22) Filed: Feb. 14, 2000

Related U.S. Application Data

(60) Provisional application No. 60/121,156, filed on Feb. 22, 1999.

(51) Int. Cl.[7] ............... A61K 31/505; A61K 31/445; C07D 239/02; C07D 419/00; C07D 213/02
(52) U.S. Cl. ............ 514/256; 514/317; 514/318; 544/298; 544/333; 544/335; 546/194; 546/208
(58) Field of Search .................. 514/256, 317, 514/318; 544/298, 333, 335; 546/194, 208

(56) References Cited

U.S. PATENT DOCUMENTS

| | | | |
|---|---|---|---|
| 4,518,711 A | 5/1985 | Hruby et al. | 514/11 |
| 4,816,586 A | 3/1989 | Portoghese | 544/340 |

FOREIGN PATENT DOCUMENTS

| | | |
|---|---|---|
| EP | 133323 | 2/1985 |
| EP | 458160 | 11/1991 |
| WO | 0014066 | 3/2000 |
| ZA | 860522 | 12/1986 |

OTHER PUBLICATIONS

Stasch et al., "4,4–Diphenylpiperidine derivatives and their sila analogues", *Arzneimittelforschung*/Drug Res., vol. 398, No. 8, 1988, pp. 1075–1078, XP002139179.

Neuser et al., "The interactions of 1–alkyl–4,4–diphenylpiperidines with opiate receptors," *Chemical Abstracts + Indexes*, US, American Chemical Society, Columbus, vol. 21, No. 98, May 23, 1983 XP002120659.

Langein et al., "Narcotic antagonists of the 4–phenylpiperidine series," *Advanced Biochem. Psychopharmacol.*, vol. 8, 1974, pp. 157–165, XP000909755.

S. Goenechea, et al, in "Investigation of the Biotransformation of Meclozine in the Human Body," *J. Clin. Chem. Clin. Biochem.*, 1988, 26(2), 105–15.

Meuldermans, W., et al "Plasma Levels, Biotransformation and Excretion of Oxatomide in Rats, Dogs, and Man," *Xenobiotica*, 1984, 15(6), 445–62.

T. Iwamoto, et al, in "Effects of KB–2796, A New Calcium Antagonist, and Other Diphenylpiperazines on [$^3$H]nitrendipine Binding", *Jpn. J. Pharmacol.*, 1988, 48(2), 241–7.

K. Natsuka, et al, in "Synthesis and Structure–Activity Relationships of 1–Substituted 4–(1,2–Diphenylethyl)piperazine Derivatives Having Narcotic Agonist and Antagonist Activity," *J. Med. Chem.*, 1987, 30(10), 1779–1787.

Primary Examiner—Mukund J. Shah
Assistant Examiner—Tamthom N. Truong
(74) Attorney, Agent, or Firm—Peter C. Richardson; Paul H. Ginsburg; Seth H. Jacobs

(57) ABSTRACT

The present invention relates to compounds of the formula I,

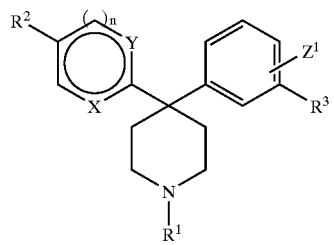

wherein $Z^1$, X, Y, $( )_n$, $R_1$, $R^2$ and $R^3$ are defined as in the specification, pharmaceutical compositions containing such compounds; and the use of such compounds to treat neurological and gastrointestinal disorders.

9 Claims, No Drawings

4-PHENYL-4-HETEROARYLPIPERIDINE DERIVATIVES

This application claims priority under 35 U.S.C. §119(e) from U.S. application Ser. No. 60/121,156, filed Feb. 22, 1999, which application is hereby incorporated by reference.

BACKGROUND OF THE INVENTION

This invention relates to 4-phenyl-4-heteroaryl derivatives which have utility as ligands or opioid receptors.

In the study of opioid biochemistry, a variety of endogenous opioid compounds and non-endogenous opioid compounds has been identified. In this effort, significant research has been focused on understanding the mechanism of opioid drug action, particularly as it relates to cellular and differentiated tissue opioid receptors.

Opioid drugs are typically classified by their binding selectivity in respect of the cellular and differentiated tissue receptors to which a specific drug species binds as a ligand. These receptors include mu ($\mu$), delta ($\delta$) and kappa ($\kappa$) receptors.

At least three subtypes of opioid receptors (mu, delta and kappa) are described and documented in the scientific literature. All three receptors are present in the central and peripheral nervous systems of many species including man. Activation of delta receptors produces antinociception in rodents and can induce analgesia in man, in addition to influencing motility of the gastrointestinal tract. (See Burks, T. F. (1995) in "The pharmacology of Opioid Peptides", edited by Tseng, L. F., Harwood Academic Publishers).

The well known narcotic opiates such as morphine and its analogs are selective for the opioid mu receptor. Mu receptors mediate analgesia, respiratory depression, and inhibition of gastrointestinal transit. Kappa receptors mediate analgesia and sedation.

The existence of the opioid delta receptor is a relatively recent discovery which followed the isolation and characterization of endogenous enkephalin peptides, which are ligands for the delta receptor. Research in the past decade has produced significant information about the delta receptor, but a clear picture of its function has not yet emerged. Delta receptors mediate analgesia, but do not appear to inhibit intestinal transit in the manner characteristic of mu receptors.

U.S. Pat. No. 4,816,586, which issued on Mar. 28, 1989 to P. S. Portoghese, refers to various delta opioid receptor antagonists. These compounds are described as possessing a unique opioid receptor antagonist profile, and include compounds that are highly selective for the delta opioid receptor.

U.S. Pat. No. 4,518,711, which issued May 21, 1985 to V. J. Hruby et al., describes cyclic, conformationally constrained analogs of enkephalins. These compounds include both agonists and antagonists for the delta receptor, and are said to induce pharmacological and therapeutic effects, such as analgesia in the case of agonist species of such compounds. The antagonist species of the disclosed compounds are suggested to be useful in the treatment of schizophrenia, Alzheimer's disease, and respiratory and cardiovascular functions.

S. Goenechea, et al, in "Investigation of the Biotransformation of Meclozine in the Human Body," *J. Clin. Chem. Clin. Biochem.*, 1988, 26(2), 105–15, describe the oral administration of a polyaryl piperazine compound in a study of meclozine metabolization in human subjects.

In "Plasma Levels, Biotransformation and Excretion of Oxatomide in Rats, Dogs, and Man," *Xenobiotica*, 1984, 15(6), 445–62, Meuldermans, W., et al. refer to a metabolic study of plasma levels, biotransformation, and excretion of oxatomide.

T. Iwamoto, et al, in "Effects of KB-2796, A New Calcium Antagonist, and Other Diphenylpiperazines on [$^3$H] nitrendipine Binding", *Jpn. J. Pharmacol.*, 1988, 48(2), 241–7, describe the effect of a polyaryl piperazine as a calcium antagonist.

K. Natsuka, et al, in "Synthesis and Structure-Activity Relationships of 1-Substituted 4-(1,2-Diphenylethyl) piperazine Derivatives Having Narcotic Agonist and Antagonist Activity," *J. Med. Chem.*, 1987, 30 (10), 1779–1787, refer to racemates and enantiomers of 1-substituted 4-[2-(3-hydroxyphenyl)-1-phenylethyl] piperazine derivatives.

European Patent Application No. 458,160, published on Nov. 27, 1991, refers to certain substituted diphenylmethane derivatives as analgesic and antiinflammatory agents, including compounds wherein the methylene bridging group (linking the two phenyl moieties) is substituted on the methylene carbon with a piperidinyl or piperazinyl group.

South African Patent Application No. 8604522, which was published on Dec. 12, 1986, refers to certain N-substituted arylalkyl and aryl-alkylene substituted amino-heterocyclic compounds, including piperidine derivatives, as cardiovascular, antihistamine, and anti-secretory agents.

European Patent Application No. 133,323, published on Feb. 20, 1985, refers to certain diphenylmethyl piperazine compounds as non-sedative antihistamines.

United States Patent Application of Spiros Liras et al., entitled "3,3-Biarylpiperidine and 2,2-Biarylmorpholine Derivatives" and filed on Dec. 28, 1998, refers to 3,3-biarylpiperidine and 2,2-biarylmorpholine derivatives having the ability to bind to opioid receptors. U.S. patent application Ser. No. 60/099,565, filed on Sep. 9, 1998, refers to 4,4-biarylpiperidine derivatives having the ability to bind to opioid receptors.

There is a continuing need in the art for improved opioid compounds, particularly compounds which are free of addictive character and other adverse side effects of conventional opiates such as morphine and pethidine.

The present inventor has discovered a novel class of 4,4-biarylpiperidine derivatives that are potent and selective delta opioid ligands and are useful for treatment of rejection in organ transplants and skin grafts, epilepsy, chronic pain, neurogenic pain, nonsomatic pain, stroke, cerebral ischemica, shock, head trauma, spinal cord trauma, brain edema, Hodgkin's disease, Sjogren's disease, systemic lupus erythematosus, gastrointestinal disorders such as gastritis, functional bowel disease, irritable bowel syndrome, functional diarrhea, functional distention, nonulcerogenic dyspepsia and other disorders of motility or secretion, and emesis, acute pain, chronic pain, neurogenic pain, nonsomatic pain, allergies, respiratory disorders such as asthma, cough and apnea, inflammatory disorders such as rheumatoid arthritis, osteoarthritis, psoriasis and inflammatory bowel disease, urogenital tract disorders such as urinary incontinence, hypoxia (e.g., perinatal hypoxia), hypoglycemic neuronal damage, chemical dependencies and addictions (eq., a dependency on, or addiction to opiates, benzodiazepines, cocaine, nicotine or ethanol), drug or alcohol withdrawal symptoms, and cerebral deficits subsequent to cardiac bypass surgery and grafting.

SUMMARY OF THE INVENTION

This invention relates to compounds of the formula

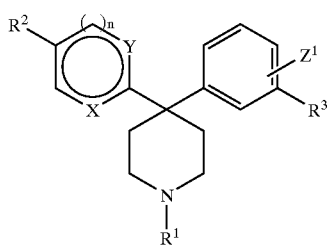

wherein X and Y are selected, independently, from oxygen, nitrogen, sulfur and CH, with the proviso that the ring containing X and Y must be aromatic and with the proviso that X and Y cannot both be either oxygen or sulfur;

( )$_n$ means $(CH_2)_n$ and n is zero or one;

$R^1$ is hydrogen, $(C_0-C_8)$alkoxy-$(C_0-C_8)$alkyl-, wherein the total number of carbon atoms is eight or less, aryl, aryl-$(C_1-C_8)$alkyl-, heteroaryl, heteroaryl-$(C_1-C_8)$alkyl-, heterocyclic, heterocyclic-$(C_1-C_8)$alkyl, $(C_3-C_7)$cycloalkyl-, or $(C_3-C_7)$cycloalkyl-$(C_1-C_8)$alkyl, wherein said aryl and the aryl moiety of said aryl-$(C_1-C_8)$alkyl- are selected, independently, from phenyl and naphthyl, and wherein said heteroaryl and the heteroaryl moiety of said heteroaryl-$(C_1-C_8)$alkyl- are selected, independently, from pyrazinyl, benzofuranyl, quinolyl, isoquinolyl, benzothienyl, isobenzofuryl, pyrazolyl, indolyl, isoindolyl, benzimidazolyl, purinyl, carbazolyl, 1,2,5-thiadiazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, oxazolyl, oxadiazolyl, isoxazolyl, thiazolyl, isothiazolyl, furanyl, pyrazolyl, pyrrolyl, tetrazolyl, triazolyl, thienyl, imidazolyl, pyridinyl, and pyrimidinyl; and wherein said heterocyclic and the heterocyclic moiety of said heterocyclic-$(C_1-C_8)$alkyl- are selected from saturated or unsaturated nonaromatic monocyclic or bicyclic ring systems, wherein said monocyclic ring systems contain from four to seven ring carbon atoms, from one to three of which may optionally be replaced with O, N or S, and wherein said bicyclic ring systems contain from seven to twelve ring carbon atoms, from one to four of which may optionally be replaced with O, N or S; and wherein any of the aryl, heteroaryl or heterocyclic moieties of $R^1$ may optionally be substituted with from one to three substituents, preferably with one or two substituents, independently selected from halo, $(C_1-C_6)$alkyl optionally substituted with from one to seven (preferably with from zero to four) fluorine atoms, phenyl, benzyl, hydroxy, acetyl, amino, cyano, nitro, $(C_1-C_6)$alkoxy, $(C_1-C_6)$alkylamino and $[(C_1-C_6)$alkyl$]_2$amino, and wherein any of alkyl moieties in $R^1$ (e.g., the alkyl moieties of alkyl, alkoxy or alkylamino groups) may optionally be substituted with from one to seven (preferably with from zero to four) fluorine atoms;

$R^2$ is hydrogen, aryl, halo, heteroaryl, heterocyclic, $SO_2R^4$, $COR^4$, $CONR^5R^6$, $COOR^4$ or $C(OH)R^5R^6$ wherein each of $R^4$, $R^5$ and $R^6$ is defined, independently, as $R^1$ is defined above, or $R^5$ and $R^6$, together with the carbon or nitrogen to which they are both attached, form a three to seven membered saturated ring containing from zero to three heterocarbons selected, independently, from O, N and S, and wherein said aryl, heteroaryl, and heterocyclic are defined as such terms are defined above in the definition of $R^1$, and wherein any of the aryl, heteroaryl and heterocyclic moieties of $R^2$ may optionally be substituted with from one to three substituents, preferably with one or two substituents, independently selected from halo, $(C_1-C_6)$alkyl optionally substituted with from one to seven (preferably with from zero to four) fluorine atoms, phenyl, benzyl, hydroxy, acetyl, amino, cyano, nitro, $(C_1-C_6)$alkoxy optionally substituted with from one to seven (preferably with from zero to four) fluorine atoms, $(C_1-C_6)$alkylamino and $[(C_1-C_6)$alkyl$]_2$amino;

$R^3$ is hydroxy, $-(C_1-C_6)$alkyl-OH, $-(C_1-C_6)$alkyl-$(C_1-C_6)$alkoxy, $NHSO_2R^7$, $C(OH)R^7R^8$, halo, or heteroaryl as defined for $R^1$ above or $CONHR^7$, wherein $R^7$ and $R^8$ are the same or different and are selected from hydrogen, $(C_1-C_4)$alkyl, $(C_1-C_4)$alkoxy and $(C_1-C_4)$alkoxy-$(C_1-C_4)$alkyl having a total of 4 or less carbon atoms, and wherein any of the alkyl moieties of $R^7$ and $R^8$ may optionally be substituted with from one to seven (preferably with from zero to four) fluorine atoms; and $Z^1$ is hydrogen, halo or $(C_1-C_5)$alkyl;

with the proviso that there are no two adjacent ring oxygen atoms and no ring oxygen atom adjacent to either a ring nitrogen atom or a ring sulfur atom in any of the heterocyclic or heteroaryl moieties of formula I; and the pharmaceutically acceptable salts of such compounds.

Preferred compounds of the formula I include those wherein n is zero or one; X and Y are both nitrogen or X is nitrogen and Y is CH or oxygen; $R^1$ is benzyl, cyclopropylmethyl, 2-pyridyl, 4-fluoro-2-pyridyl, pyrimidyl, 2-methylpentyl, 3-phenylpropyl, 2ethoxyethyl or 3,5,5-trimethylhexyl; $R^2$ is $CON(CH_2CH_3)_2$, $CON(CH_3)_2$, $CON(CH_2CH_3)CH_3$, $C(OH)(CH_3)_2$, $C(OH)(CH_2CH_3)_2$, 3,3dimethyloxazoline, 3,3-diethyloxazoline, benzoxazole, tetrazole or 3,5-dimethylpyrazole; and $R_3$ is OH, $CONH_2$, fluoro, bromo, chloro, iodo, or $NHSO_2R^7$. In one embodiment of the preferred compounds, n is zero, Y is CH, and $R^3$ is OH or $CONH_2$.

The compounds of formula I and their pharmaceutically acceptable salts are opioid receptor ligands and are useful in the treatment of a variety of neurological and gastrointestinal disorders. Examples of disorders that can be treated with the compounds of formula I and their pharmaceutically acceptable salts are rejection in organ transplants and skin grafts, epilepsy, chronic pain, neurogenic pain, nonsomatic pain, stroke, cerebral ischemica, shock, head trauma, spinal cord trauma, brain edema, Hodgkin's disease, Sjogren's disease, systemic lupus erythematosus, gastrointestinal disorders such as gastritis, functional bowel disease, irritable bowel syndrome, functional diarrhea, functional distention, nonulcerogenic dyspepsia and other disorders of motility or secretion, and emesis, acute pain, chronic pain, neurogenic pain, nonsomatic pain, allergies, respiratory disorders such as asthma, cough and apnea, inflammatory disorders such as rheumatoid arthritis, osteoarthritis, psoriasis and inflammatory bowel disease, urogenital tract disorders such as urinary incontinence, hypoxia (e.g., perinatal hypoxia), hypoglycemic neuronal damage, chemical dependencies and addictions (e.g., a dependency on, or addiction to opiates, benzodiazepines, cocaine, nicotine or ethanol), drug or alcohol withdrawal symptoms, and cerebral deficits subsequent to cardiac bypass surgery and grafting.

The present invention also relates to the pharmaceutically acceptable acid addition and base addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, ptoluenesulfonate and pamoate [i.e., 1,1'-methylene-bis-(2-hydroxy-3-naphthoate)]salts. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc.

The present invention also relates to the pharmaceutically acceptable base addition salts of compounds of the formula I. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc.

For a review on pharmaceutically acceptable salts, see Berge et al., J. Pharm. Sci., 66, 1–19 (1977).

This invention also relates to a pharmaceutical composition for treating a disorder or condition, the treatment or prevention of which can be effected or facilitated by modulating (i.e., increasing or decreasing) binding to opioid receptors in a mammal, including a human, comprising an amount of a compound of the formula I, or a pharmaceutically effective salt thereof, that is effective in treating such disorder or condition and a pharmaceutically acceptable carrier.

This invention also relates to a method of treating a disorder or condition, the treatment of which can be effected or facilitated by modulating binding to opioid receptors in a mammal, comprising administering to a mammal in need of such treatment an amount of a compound of the formula I, or a pharmaceutically effective salt thereof, that is effective in treating such disorder or condition.

This invention also relates to a pharmaceutical composition for treating a disorder or condition selected from inflammatory diseases such as arthritis (e.g., rheumatoid arthritis and osteoarthritis), psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e addictions to or dependencies on alcohol, opiates, benzodiazepines, nicotine, heroin or cocaine), chronic pain, nonsomatic pain, acute pain and neurogenic pain, systemic lupus erythematosus, Hodgkin's disease, Sjogren's disease, epilepsy and rejection in organ transplants and skin grafts in a mammal, including a human, comprising a glutamate neurotransmission modulating effective amount of a compound of the formula I, or a pharmaceutically salt thereof, and a pharmaceutically acceptable carrier.

This invention also relates to a method for treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosus, Hodgkin's disease, Sjogren's disease, epilepsy and rejection in organ transplants and skin grafts, in a mammal, comprising administering to such mammal, including a human, an opioid receptor binding modulating effective amount of a compound of the formula I, or a pharmaceutically acceptable salt thereof.

This invention also relates to a pharmaceutical composition for treating a disorder or condition, the treatment of which can be effected or facilitated by modulating binding to opioid receptors in a mammal, including a human, comprising an opioid receptor binding modulating effective amount of a compound of the formula I, or a pharmaceutically acceptable salt thereof, and a pharmaceutically acceptable carrier.

This invention also relates to a method for treating a disorder or condition, the treatment of which can be effected or facilitated by modulating in a mammal, including a human, comprising administering to such mammal an opioid receptor binding modulating effective amount of a compound of the formula I or a pharmaceutically acceptable salt thereof.

This invention also relates to a method of treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosus, Hodgkin's disease, Sjogren's disease, epilepsy and rejection in organ transplants and skin grafts in a mammal, comprising administering to a mammal in need of such treatment an amount of a compound of the formula I that is effective in treating such condition.

This invention also relates to a pharmaceutical composition for treating a condition selected from inflammatory diseases such as arthritis, psoriasis, asthma, or inflammatory bowel disease, disorders of respiratory function such as asthma, cough and apnea, allergies, gastrointestinal disorders such as gastritis, functional bowel disease, irritable bowel syndrome, functional diarrhea, functional distension, functional pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions (e.g., addictions to or dependencies on alcohol, opiates, benzodiazepines, nicotine, heroin or cocaine), chronic pain, nonsomatic pain, acute pain and neurogenic pain, systemic lupus erythematosus, Hodgkin's disease, Sjogren's disease, epilepsy and rejection in organ transplants and skin grafts in a mammal, comprising an amount of a compound of the formula I that is effective in treating such condition and a pharmaceutically acceptable carrier.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

The term "alkoxy", as used herein, means "—O-alkyl", wherein "alkyl" is defined as above.

The term "alkylene", as used herein, means an alkyl group having two available binding sites (i.e., -alkyl-, wherein alkyl is defined as above).

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula I may have chiral centers and therefore may exist in different enantiomeric and diastereomic forms. This invention relates to all optical isomers and all other stereoisomers of compounds of the formula I, and to all racemic and other mixtures thereof, and to all pharmaceutical compositions and methods of treatment defined above that contain or employ such isomers or mixtures.

Formula I above includes compounds identical to those depicted but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies.

This invention also relates to compounds of the formula

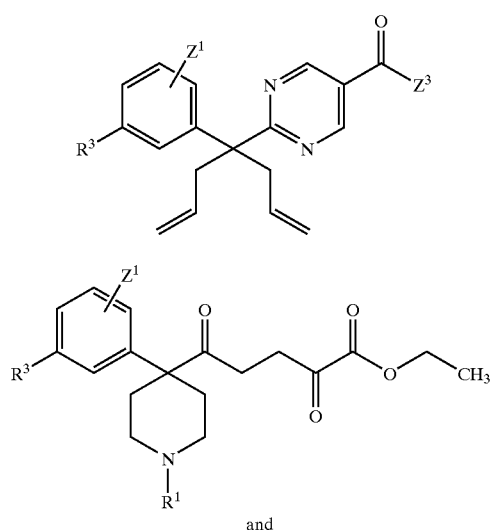

and

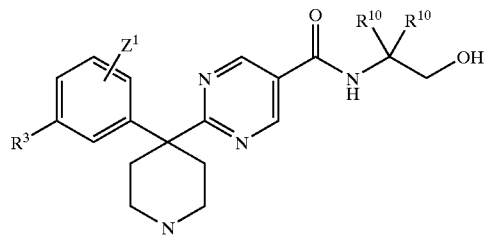

wherein $Z^3$ is hydrogen or $OR^{10}$ wherein $R^{10}$ is ($C_1$–$C_6$) alkyl, and wherein $Z^1$ and $R^3$ are defined as above for formula I. These compounds are useful as intermediates in the synthesis compounds of the formula I.

DETAILED DESCRIPTION OF THE INVENTION

The compounds of formula I can be prepared according to the methods illustrated in Schemes 1–12 and discussed below. In the reaction schemes and discussion that follow, unless otherwise indicated, $R_1$, $R^2$, $R^3$, $R^4$, and structural formula I are defined as above. Also, throughout this document, the abbreviation "Me" is used to mean "methyl", and "EC" is used to mean "ethyl". Scheme 1 illustrates a method for the preparation of compounds with the general structural formula I defined as above.

Scheme 1 illustrates a method for the preparation of compounds with the general formula I wherein n=1, X=N, Y=N, $R^3$ is ($C_1$–$C_6$)alkoxy or fluorine, $R^2$ is $CONR^5R^6$ and $R^1$ is as defined above with the proviso that it is not attached to the piperidine nitrogen at a secondary alkyl carbon or an aryl group. Referring to Scheme 1, a benzyl nitrile derivative of formula 0, wherein $R^3$ is methoxy or fluorine, is heated with a allyl halide and aqueous sodium hydroxide in the presence of a phase transfer catalyst (PTC) at temperatures ranging from 30° C. to 110° C., preferably at about the reflux temperature to produce the corresponding compound of formula 1. Treatment of a compound of formula 1 with a trialkyl aluminum reagent and ammonium chloride in solvents such as methylene chloride or dichloroethane at temperatures ranging from 30° C. to 100° C., preferably at about the reflux temperature, to produce the corresponding amidine derivative of formula 2.

Alternatively, the nitrile derivative 1 can be treated with sodium or potassium amide in solvents such as dimethylformamide or glycol at temperatures ranging from 50° C. to 150° C., preferably at about reflux, to produce the corresponding amidine derivative of formula 2.

The compound of formula 2, produced by either of the above methods, is treated with 2-dimethylaminomethylene-1,3-bis(dimethylimmonio)propane bisperchlorate and sodium ethoxide in ethanol at temperatures ranging from 30° C. to 95° C., preferably at about reflux, to produce the corresponding pyrimidine carboxaldehyde derivative of formula 3.

The compound of formula 3 is oxidized by sodium chlorite in the presence of a suitable buffer such as potassium phosphate monobasic, a hypochlorite scavenger such as 2-methyl-2-butene and an alcoholic solvent such as tert-butanol, to produce the corresponding carboxylic acid. This reaction is performed at temperatures ranging from −10° C. to 30° C., preferably at about room temperature.

Alternatively, the oxidation can be carried out using other suitable oxidants such as potassium permanganate or pyridinium dichlorochromate (PDC), at temperatures ranging from 30° C. to 100° C., to produce the corresponding carboxylic acid.

The carboxylic acid derivative produced by either of the above methods is then treated with cyclohexyl carbodiimide (DCC) and methanol in solvents such as chloroform, dichloromethane or dichloroethane, at temperatures ranging from 30° C. to 100° C., preferably at about room temperature, to produce the corresponding ester derivative of formula 4.

Alternatively, the carboxylic acid derivative can be treated with either trimethylsilyl diazomethane and methanol, or acetyl chloride and methanol, at temperatures ranging from 30° C. to 75° C., preferably at about room temperature, to produce the ester derivative of formula 4.

Oxidative cleavage of the olefins in the ester derivative of formula 4 was carried out using osmium tetroxide and a suitable co-catalyst such as N-methylmorpholine N-oxide (NMO), in a solvent mixture consisting of acetone and water, at temperatures ranging from −5° C. to 50° C., preferably at about room temperature, producing the corresponding tetra-ol derivative. The tetraol derivative prepared above was treated with a suitable oxidizing agent such as sodium periodate in an alcohol/water mixture, producing the corresponding di-aldehyde. The crude dialdehyde prepared above was treated with a primary amine and a suitable boro-hydride reagent such as sodium triacetoxyborohydride, in solvents such as dichloromethane or dichloroethane, at temperatures ranging from 0° C. to 50° C., preferably at about room temperature, to produce the corresponding piperidine derivative of formula 5.

Treatment of the ester of formula 5 with an aluminum amide of a primary or secondary amine, for example, diethyl amine, in a solvent such as dichloroethane or toluene, at a temperature ranging from about 20° C. to about the reflux temperature, preferably at about the reflux temperature, yields the corresponding amide of formula 6. Alternatively, the amide of formula 6 can be prepared via the acid 5a by hydrolysis of the ester 5 with a suitable alkali metal hydroxide such as lithium or sodium hydroxide, at temperatures ranging from 0° C. to about room temperature, preferably at about room temperature. Treatment of the acid of formula 5a with a suitable primary or secondary amine, such as diethyl amine and 1,1'-carbonyldiimidazole (CDI), in solvents such as dichloromethane or dichloroethane, at temperatures ranging from 0° C. to about room temperature, preferably at about room temperature, which yields the corresponding amide of formula 6.

SCHEME 1

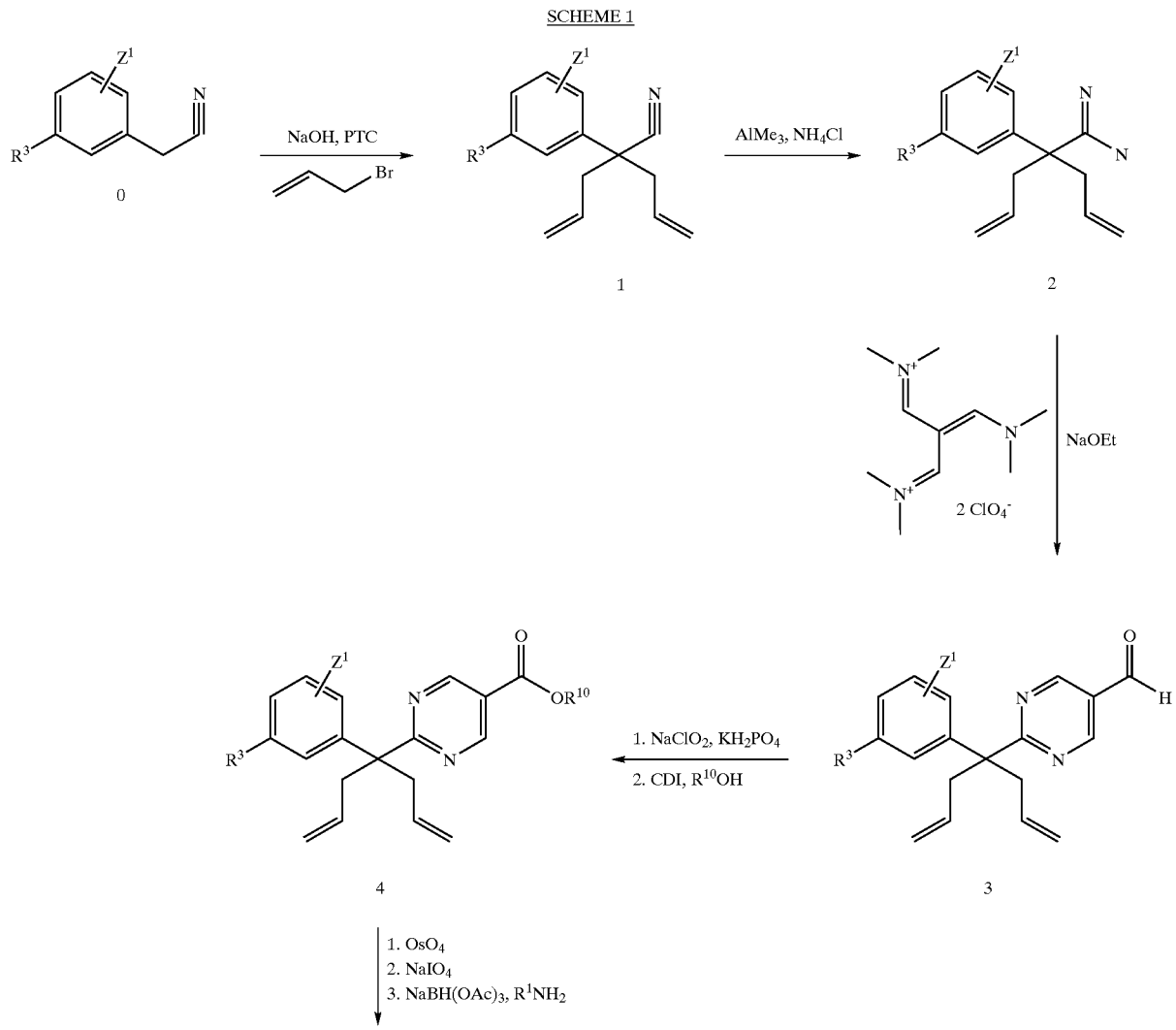

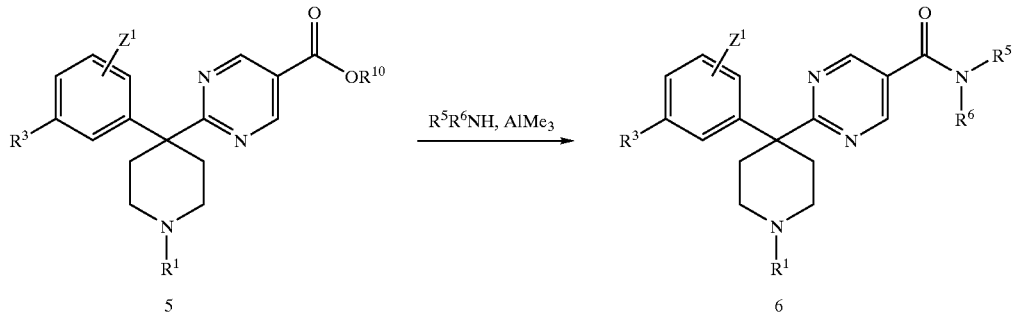

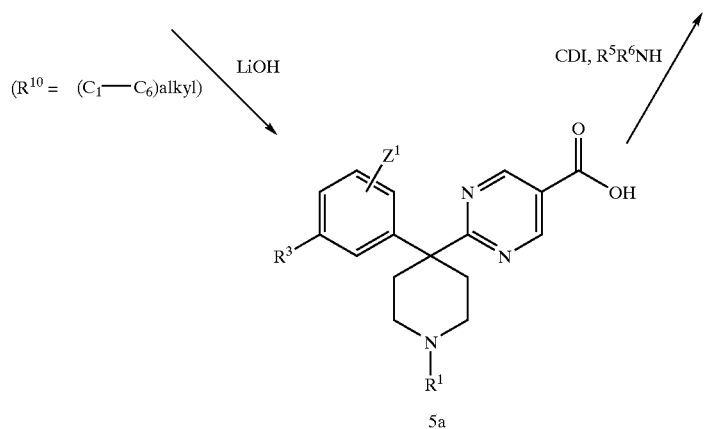

Compounds of the general formula I where $R^3$ is hydroxy can be prepared by deprotecting the corresponding alkyl ether of formula 7 (wherein $R_{10}$ is $(C_1-C_6)$alkyl) with boron tribromide or boron trichloride in dichloromethane, or with aqueous hydrobromic acid and acetic acid, or with sodium ethanethiolate in dimethylformamide, at a temperature ranging from about 0° C. to the reflux temperature, producing the corresponding phenols of formula 8, as shown in Scheme 2. Room temperature is preferred when boron tribromide (BBr$_3$) is used, the reflux temperature is preferred when hydrobromic acid/acetic acid is used, and about 100° C. to about 120° C. is preferred when sodium ethanmethiolate is used.

SCHEME 2

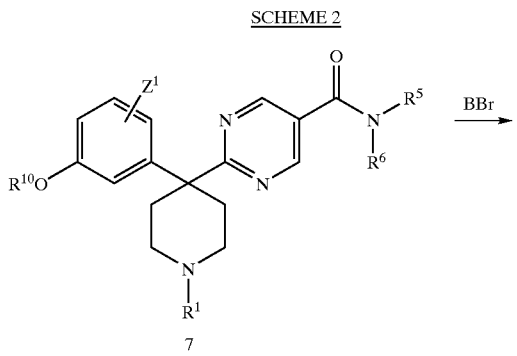

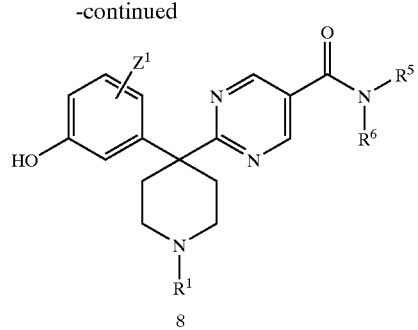

Variations in the nature of the $R^1$ group on the piperidine nitrogen can be affected in the following manner, as illustrated by process steps (9→10→11) in scheme 3. Treatment of the benzyl amine of formula 9 with 1-chloroethylchloroformate (ACECl), in solvents such as dichloromethane or dichloroethane, at temperatures ranging from about 20° C. to the reflux temperature, preferable at about reflux, following treatment with methanol at temperatures ranging from about 20° C. to the reflux temperature, preferably at about reflux, yields the corresponding secondary amine of formula 10.

Treatment of the compound of formula 10 with an aldehyde and sodium triacetoxyborohydride or another reducing agent (e.g., sodium borohydride or sodium cyanoborohydride), in dichloromethane, 1,2 dichloroethane or another suitable solvent such as methanol, ethanol or toluene, at a temperature ranging from about 0° C. to 100° C., preferably at about room temperature, yields the desired compound of formula 11.

SCHEME 3

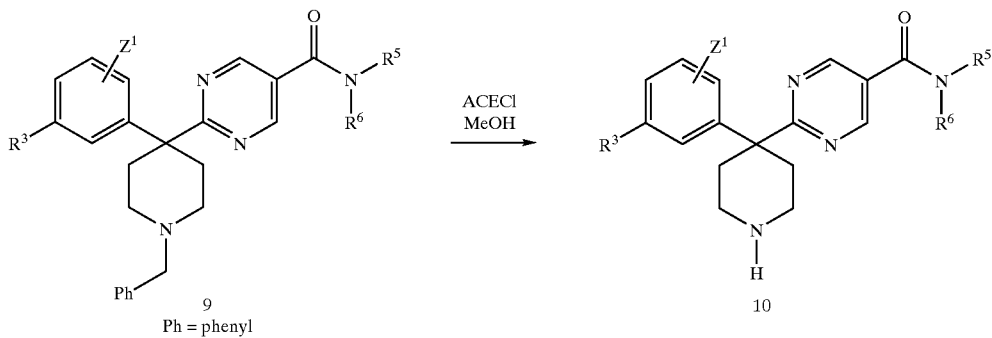

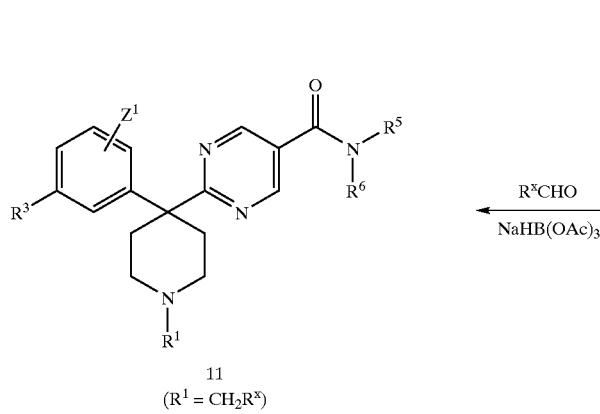

Compounds of formula I wherein R¹ is a group that attaches to the piperidine nitrogen via an aryl moiety or a primary or secondary alkyl moiety, can be prepared by treating the corresponding compound of formula 10 with an alkylating or arylating agent of the formula R¹X, wherein X is a leaving group such as chloro, bromo, iodo, triflate (OTf), mesylate (OMs) or tosylate (OTs), and sodium or potassium carbonate or another alkali metal carbonate or bicarbonate in a solvent such as dimethylformamide, dichloromethane or 1,2 dichloroethane, at a temperature ranging from about 20° C. to 100° C., to produce the desired compound of formula 11, as shown below in Scheme 4.

SCHEME 4

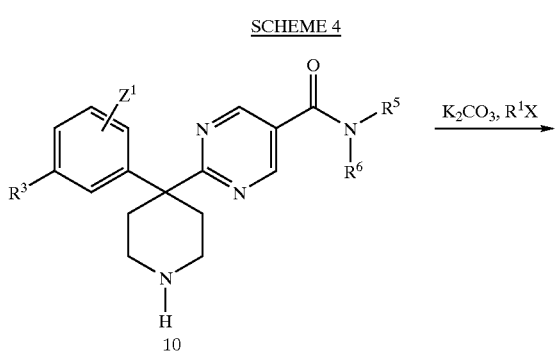

-continued

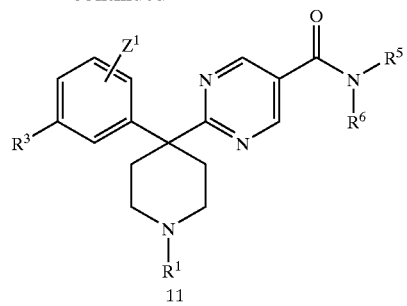

Compounds of the general formula I where R³=CONHR can be prepared from the corresponding phenols of formula 11 as illustrated in Scheme 5 below. The compound of formula 8 is treated with trifluoromethane sulfonic anhydride or another suitable reagent such as N-phenyltrifluoromethanesulfonimide, in the presence of a base such as pyridine, triethylamine, another trialkyl amine, an alkali metal hydride or an alkali metal carbonate, to form the trifluoromethane sulfonate ester of formula 11. This reaction is typically performed in dichloromethane at a temperature ranging from about 0° C. to the reflux temperature, preferably at about room temperature. Treatment of the triflate of formula 11 with zinc cyanide and a suitable palladium catalyst (e.g., tetrakis triphenylphosine palladium) in dimethylformamide, at temperatures ranging from about 20° C. to about the reflux temperature, preferably at about the reflux temperature, produced the corresponding phenyl nitrile of formula 12.

The nitrile of formula 12 was then treated with hydrogen peroxide and an alkali metal carbonate (e.g., sodium carbonate) in a lower alkanol, such as methanol or ethanol, at temperatures ranging from 0° C. to about room temperature, preferably at about room temperature, which yielded the corresponding carboxamide of formula 13. Treatment of the nitrile of formula 12 with azidotrimethylsilane ($TMSN_3$) and a dialkyl tin oxide (e.g., dibutyltin oxide) in toluene, at temperatures ranging from about 20° C. to about the reflux temperature, preferably at about reflux, produced the corresponding tetrazole of formula 14.

The compound of formula 11 is placed under a carbon monoxide atmosphere at a pressure ranging from about 14 to 100 psi, in a solution of dimethylsulfoxide and a lower alkanol such as methanol or ethanol, with a suitable trialkylamine base (e.g, triethylamine) and palladium acetate with 1,3-bis(diphenylphosphino)propane (DPPP) or another suitable palladium ligand, to produce the corresponding ester of formula 15 (scheme 6). Other suitable palladium catalysts such as bis(triphenylphosphine) palladium dichloride may also be used. This reaction is performed at temperatures ranging from about 20° C. to 100° C. Hydrolysis of the ester of formula 15 using an alkali metal hydroxide (e.g., lithium hydroxide), at temperatures ranging from 0° C. to about room temperature, preferably at about room temperature, yielded the acid of formula 16. Treatment of the acid of

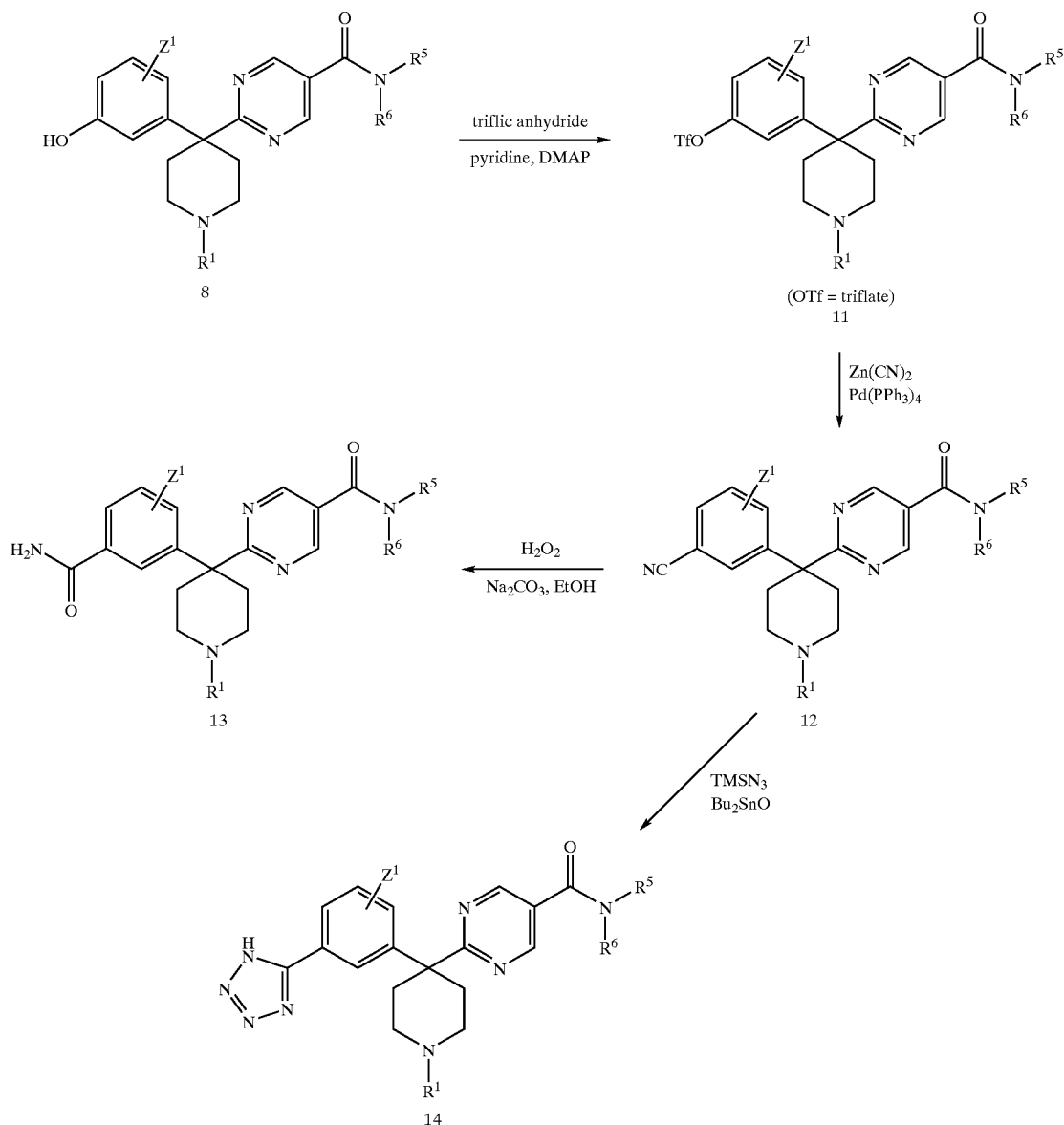

SCHEME 5

Compounds of the general formula I, where $R^3$=($C_1$–$C_6$) alkyl-OH or C(OH)$R^7R^8$ can be prepared from the corresponding phenol of formula 11 as illustrated in scheme 6.

formula 16 with a suitable alkyl chloroformate (e.g., ethyl chloroformate), at temperatures ranging from 0° C. to about room temperature, preferably at about room temperature, produced the desired mixed anhydride, which upon reduction with a suitable boro-hydride reagent (e.g., sodium borohydride), at temperatures ranging from −5° C. to about room temperature, preferably at about room temperature, produced the corresponding benzylic alcohol of formula 17. Oxidation of the benzylic alcohol of formula 17 with tetrapropyl ammonium perruthenate (TPAP), and N-methyl-morpholine-N-oxide (NMO), or some other suitable tertiary amine oxide co-oxidant, in dichloromethane or dichloroethane, at temperatures ranging from 0° C. to about room temperature, preferably at about room temperature, produced the corresponding benzaldehyde derivative. Other suitable oxidants, such as manganese dioxide, pyridinium chlorochromate or oxalyl chloride/DMSO may also be used. Treatment of the aldehyde derivative prepared above with an alkyl or aryl lithium or magnesium reagent (e.g., methyl magnesium bromide), in tetrahydrofuran, at temperatures ranging from −78° C. to about room temperature, preferably at about 0° C., yielded the corresponding benzylic alcohol of formula 18.

Compounds of the general formula I, where $R^2$=oxazolines, can be prepared from the corresponding carboxylic acid of formula 5a as illustrated in scheme 7. Treatment of the carboxylic acid of formula 5a with oxalyl chloride and a suitable amino alcohol, in dichloromethane or dichloroethane, at temperatures ranging from 0° C. to about room temperature, preferably at about room temperature, produced the desired hydroxy amide of formula 19. Treatment of the hydroxy amide of formula 19 with diethylazodicarboxylate (DEAD) and triphenylphosphine in tetrahydrofuran, at temperatures ranging from 0° C. to about room temperature, preferably at about room temperature, produced the corresponding oxazoline of formula 20. Alternatively, the hydroxy amide of formula 19 could also be treated with thionyl chloride or triflic anhydride, in solvents such as dichloromethane or dichloroethane, at temperatures ranging from 0° C. to room temperature, preferably at about room temperature, to yield the oxazoline of formula 20.

SCHEME 6

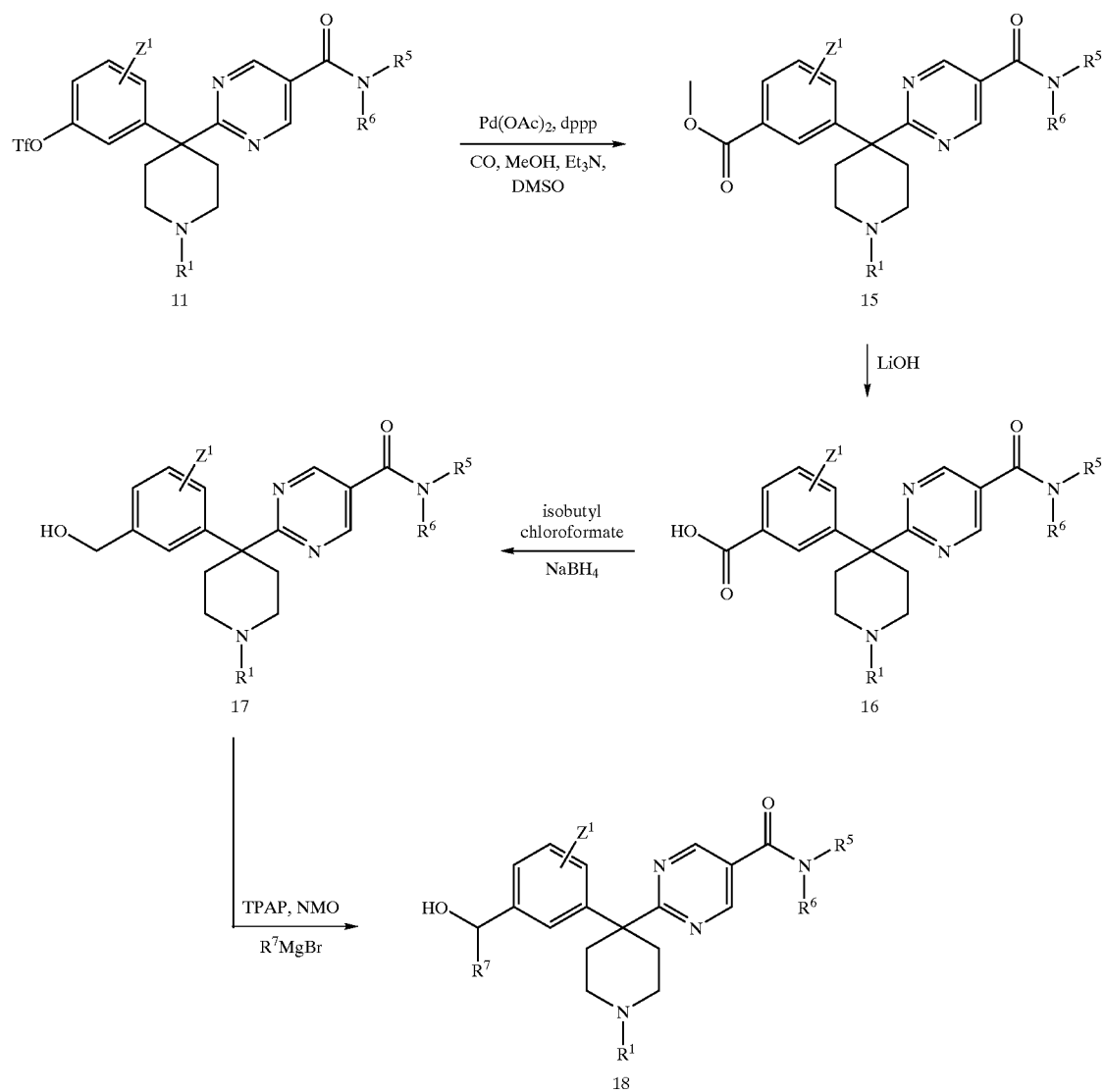

SCHEME 7

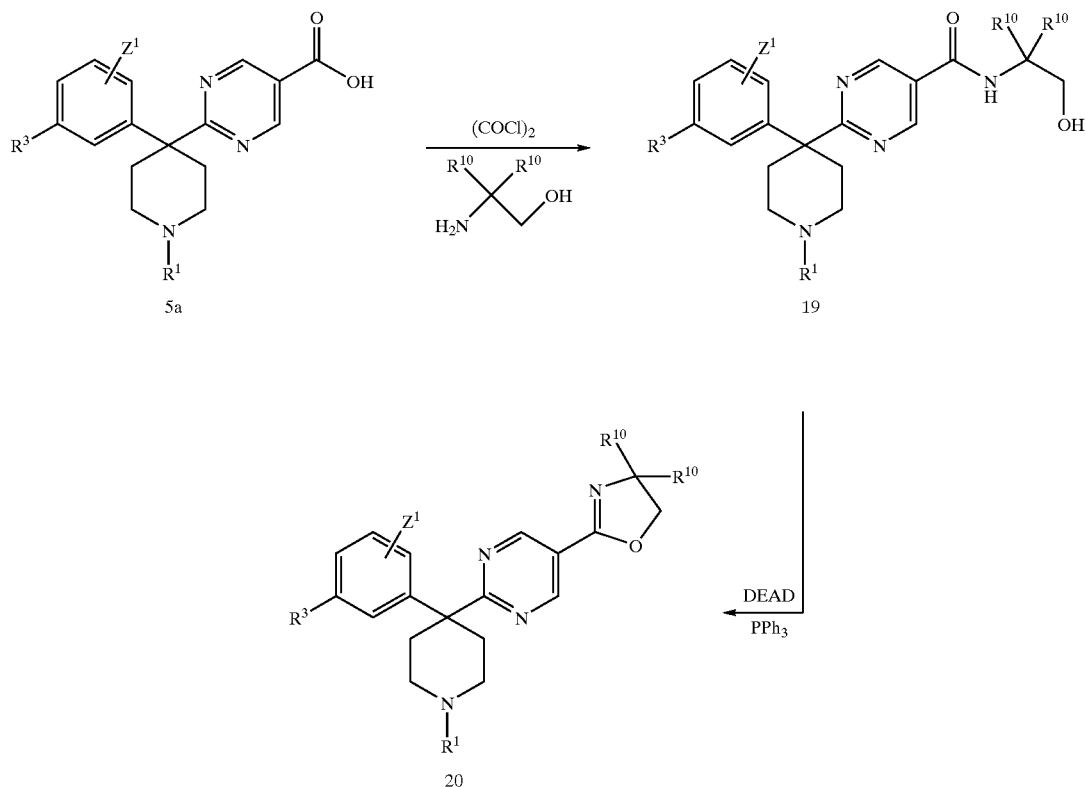

Treatment of the ester of formula 5 (scheme 8) with an alkyl or aryl organo lithium or magnesium reagent (e.g., ethyl magnesium bromide) in tetrahydrofuran, at temperatures ranging from −78° C. to about room temperature, preferably at about 0° C., produced the correspond alkyl carbinol of formula 21. Alternatively, the ester of formula 5 could be treated with a trialkyl aluminum reagent (e.g., triethyl aluminum), in solvents such as dichloromethane or dichloroethane, at temperatures ranging from room temperature to about the reflux temperature, preferably at about the reflux temperature, to yield the carbinol of formula 21.

SCHEME 8

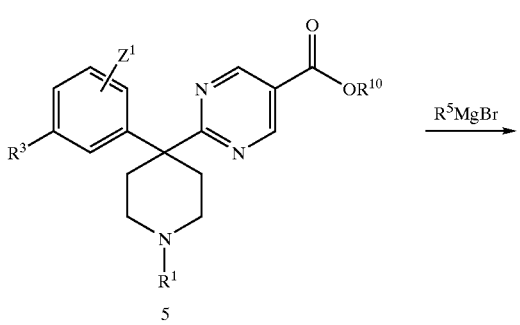

-continued

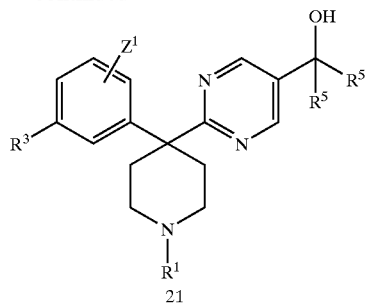

Compounds of the general formula I, where $R^3$=NHSO$_2$R$^7$, can be prepared from the corresponding carboxylic acid derivative of formula 16 as illustrated in scheme 9. Treatment of the carboxylic acid of formula 16 with diphenylphosphoryl azide (DPPA) and a suitable trialkyl amine base [e.g., triethyl amine (TEA)] in toluene, at temperatures ranging from room temperature to about the reflux temperature, preferably at about the reflux temperature, and after acidic hydrolysis, yielded the corresponding amine derivative of formula 22. Alternatively, the carboxylic acid of formula 16 could be treated with oxalyl chloride or thionyl chloride, followed by sodium azide, in solvents such as dichloromethane or dichloroethane at temperatures ranging from room temperature to about the reflux temperature, to produce the amine derivative of formula 22.

Treatment of the amine derivative of formula 22 with alkyl or aryl sulfonyl chlorides (e.g., methane sulfonyl chloride) and a amine base (e.g., pyridine) in solvents such as dichloromethane and dichloroethane, at temperatures ranging from −5° C. to about room temperature, preferably at about room temperature, yielded the sulfonamide derivative of formula 23.

triphenylphosphine and DEAD in dichloromethane or tetrahydrofuran at room temperature. Compound 27 can be subsequently oxidized to the corresponding thiazole or oxazole 28 by treatment with t-butyl perbenzoate, copper bromide and copper acetate or palladium acetate in benzene

SCHEME 9

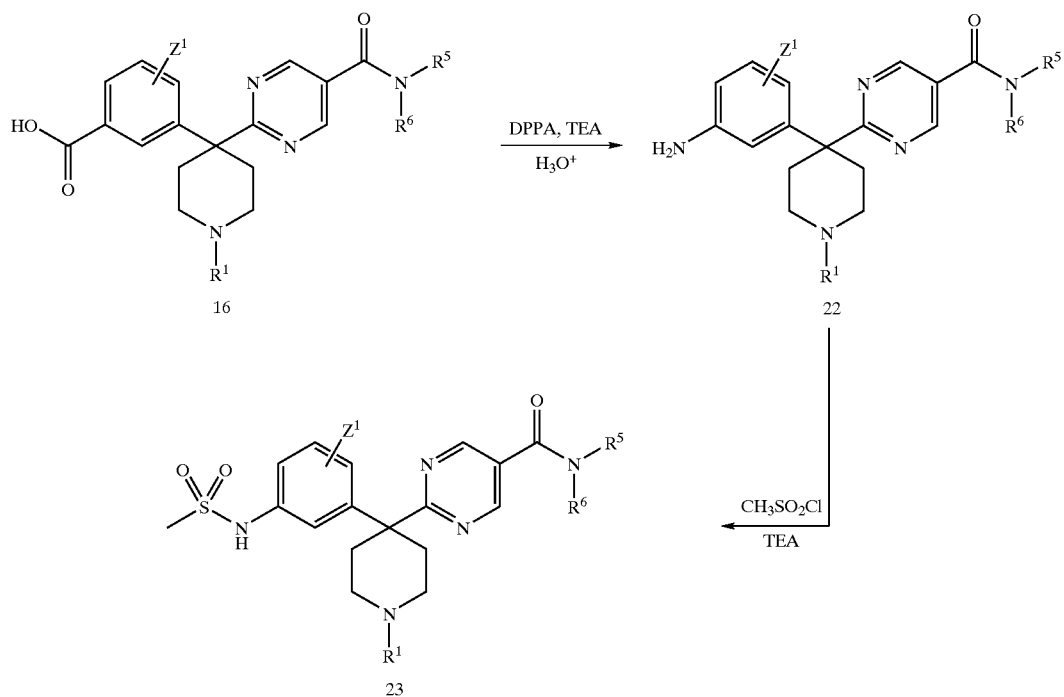

The following scheme describes methods for the preparation of compounds of the general formula wherein n=0, X=O or S, Y=N, $R^3$=OH and $R^2$=CONR$^5$R$^6$. Specifically carboxylic acid 24 prepared by standard methods can be converted to acid chloride 25 by treatment with thionyl or oxalyl chloride at preferably the reflux temperature. The acid chloride can be converted to the corresponding amide 26 by treatment with serine or cysteine methyl ester and triethylamine or other trialkylamines in solvents including dichloromethane and toluene at preferably room temperature. The amide 26 can be subsequently converted to oxazoline or thiazoline 27 by refluxing in thionyl chloride or under the influence of triflic anhydride and pyridine in dichloromethane at room temperature or under the influence of at the reflux temperature. The ester of oxazole or thiazole 28 can be transformed to the corresponding amide 29 with the methods illustrated in the previous schemes. Deprotection of the methyl ether 29 to the phenol 30 can be accomplished with the procedures outlined in the foregoing schemes. Compound 30 can be converted to a compound of formula I ($R^3$=CONH$_2$, CH$_2$OH, NHSO$_2$Me, tetrazoyl) with the methods illustrated in the foregoing schemes. Similarly, the ester 28 can be converted to a carbinol with the procedures illustrated above for the synthesis of carbine 21. In addition, ester 28 can be converted to an oxazoline with the procedures illustrated above for the synthesis of oxazoline 20.

SCHEME 10

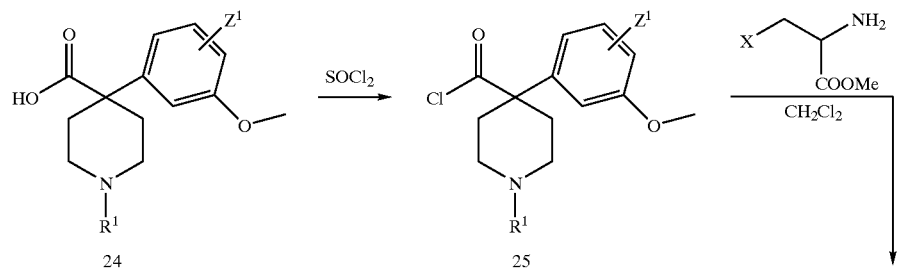

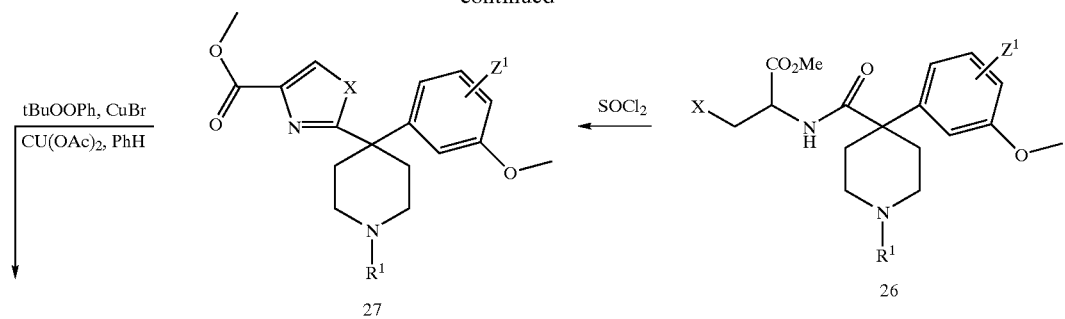

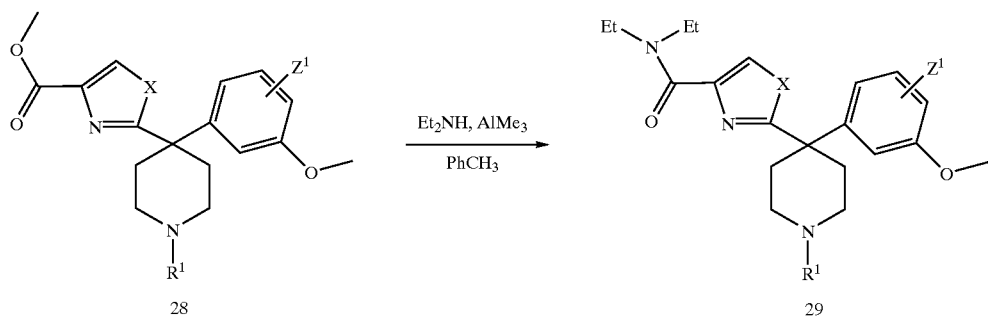

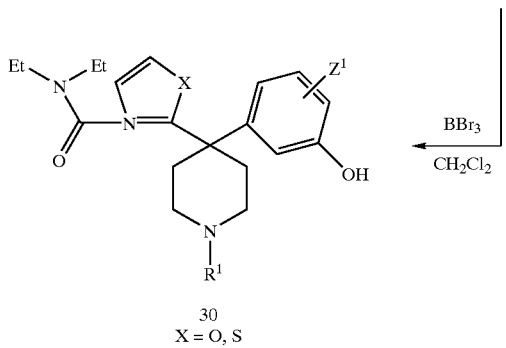

30
X = O, S

The following scheme describes methods for the preparation of compounds of the general formula I where n=0 and X=CH and Y=N. Bis-alkylation of the nitrile of formula 0 with a suitable alkylating agent such as methchloroamine hydrochloride as previously described for the preparation of compound 1 (scheme 1) yields the desired piperidine derivative of formula 31. Treatment of the nitrile of formula 31 with methyl magnesium bromide in solvents such as tetrahydrofuran or ethyl ether, at temperatures ranging from −78° C. to room temperature, preferably near room temperature, produced the ketone of formula 32. Treatment of the ketone of formula 32 with a suitable base such as lithium diethylamide and a bromopyruvate derivative, such as ethyl bromopyruvate, in solvents such as tetrahydrofuran, at temperatures ranging from −78° C. to room temperature, preferably near room temperature, produced the desired di-ketone derivative of formula 33. Compound 33 can be subsequently cyclized with ammonium acetate to produce the pyrrole of formula 34. Formation of corresponding amide from the ester 34 can be accomplished as previously described for the preparation of compound 3 (scheme 1). Compound 35 can be converted to a compound of formula I ($R^3$=CONH$_2$, CH$_2$OH, NHSO$_2$Me, tetrazoyl) with the methods illustrated in the foregoing schemes. Similarly, the ester 34 can be converted to a carbinol with the procedures illustrated above for the synthesis of carbinol 21. In addition, ester 34 can be converted to an oxazoline with the procedures illustrated above for the synthesis of oxazoline 20.

SCHEME 11

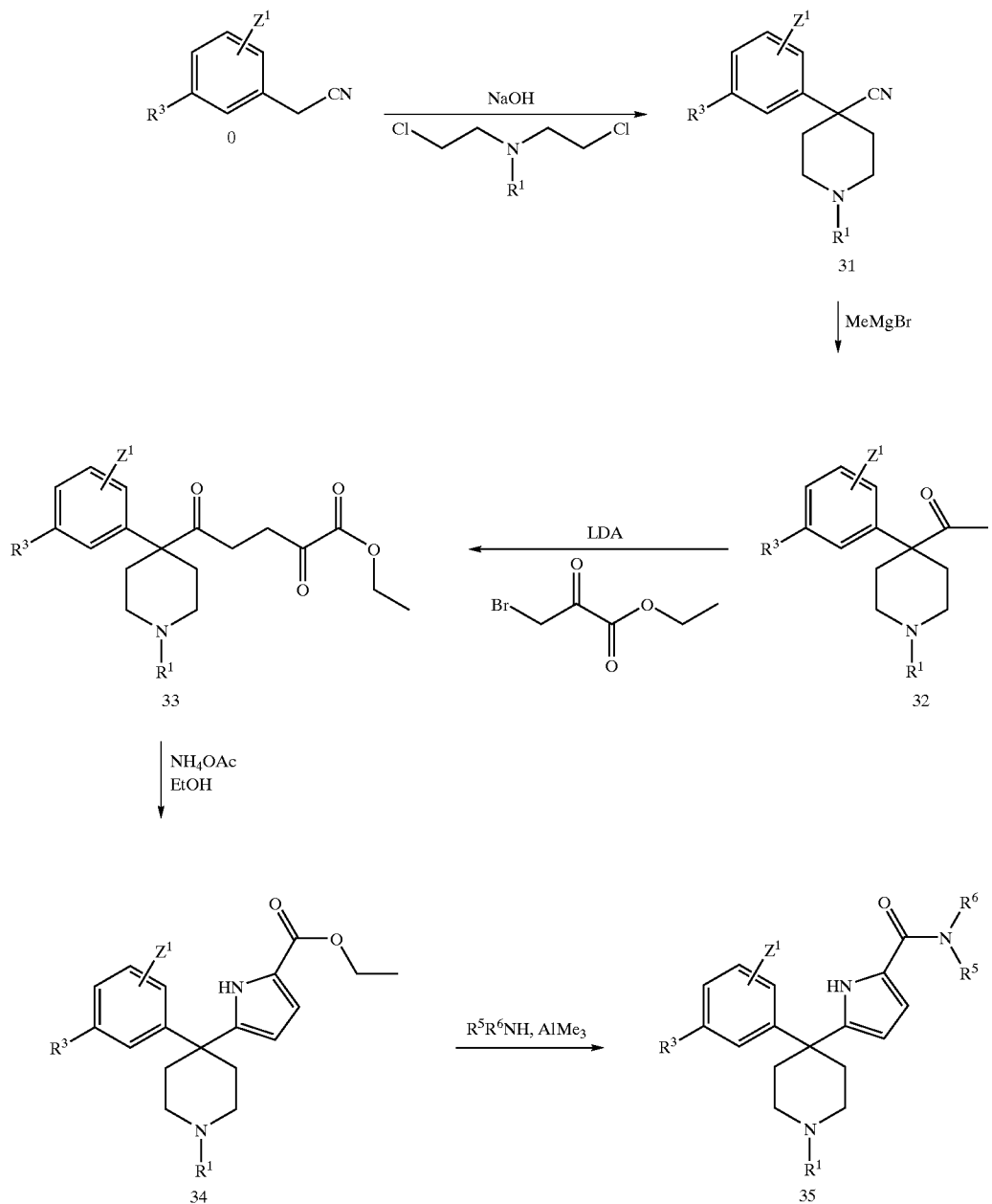

The following scheme describes methods for the preparation of compounds of the general formula I where n=1 and X=CH and Y=N. Treatment of the styrene derivative 36 with a suitable base such as n-BuLi, sec-BuLi or t-BuLi, at temperatures ranging from −78° C. to room temperature, followed by a suitably substituted 2-fluoropyridine derivative of type 37, ($R^2$=H, F, Br, $C_1$–$C_4$ alkoxy, $CO_2R^4$, $CONR^5R^6$) produced the desired diaryl enamine of type 38. Subsequent reduction of 38 with a suitable reducing agent such as $NaBH_4$, $LiAlH_4$ or $H_2$/Pd, produced the desired diarylpiperidine 39. The compound of general formula 39 ($R^1$=H) can be obtained by reductive alkylation as previously described for compound 11 (scheme 3). The ester derivative of formula 39 ($R^2$=$CO_2R^4$) can be obtained by reaction with a suitable palladium catalyst as previously described for compound 15 (scheme 6). The amide derivative of formula 39 ($R^2$=$CONR^5R^6$) can be obtained by reaction with a suitable aluminum amide reagent as described previously for the preparation of compound 6 (scheme 1). Compound 39 can be converted to a compound of formula I ($R^3$=$CONH_2$, $CH_2OH$, $NHSO_2Me$, tetrazoyl) with the methods illustrated in the foregoing schemes. In addition, ester 39 ($R^2$=$CO_2R^4$) can be converted to an oxazoline with the procedures illustrated above for the synthesis of oxazoline 20.

SCHEME 12

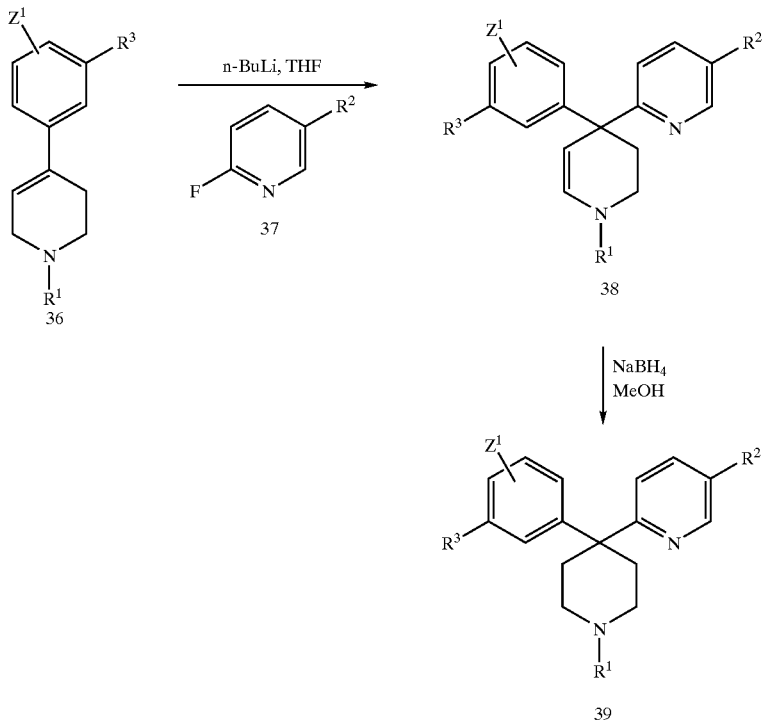

The preferred method of making compounds of the formula I wherein $R^3$ is OH, $NHSO_2R^7$, $C(OH)R^7R^8$ or $C(=O)NHR^7$ is to make the analogous compounds wherein $R^3$ is O—$(C_1-C_6)$alkyl and then derivatize them using standard methods well known in art and illustrated in the foregoing schemes.

The starting materials used in the processes of Schemes 1–12 are either commercially available, known in the literature, or readily obtainable from commercially available or known compounds using methods that are well known in the art or described above.

Unless indicated otherwise, the pressure of each of the above reactions is not critical. Generally, the reactions will be conducted at a pressure from about one to about three atmospheres, preferably at ambient pressure (about one atmosphere).

The preparation of other compounds of the formula I not specifically described in the foregoing experimental section can be accomplished using combinations of the reactions described above that will be apparent to those skilled in the art.

The compounds of the formula I that are basic in nature are capable of forming a wide variety of different salts with various inorganic and organic acids. The acid that can be used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

Compounds of the formula that are acidic in nature are capable of forming base salts with various pharmacologically acceptable cations. These salts are all prepared by conventional techniques. The chemical bases that are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the formula I and the pharmaceutically acceptable salts thereof (hereinafter, also referred to, collectively, as "the active compounds of the invention") are useful for the treatment of neurodegenerative, psychotropic and drug or alcohol induced deficits and are potent opioid receptor ligands. The active compounds of the invention may therefore be used in the treatment of disorders and conditions, such as those enumerated above, that can be treated by modulating binding to an opioid receptor.

The ability of the compounds of formula I to bind to the various opioid receptors and their functional activity at such receptors can be determined as described below. Binding to the delta opioid receptor can be determined using procedures well known in the art, such as those referred to by Lei Fang et al., *J. Pharm. Exp. Ther.*, 268 1994 836–846 and Contreras et al., *Brain Research*, 604, 1993, 160–164.

In the description of binding and functional assays that follows, the following abbreviations and terminology are used.

DAMGO is [D-Ala2,N-MePhe4,Gly5-ol]enkephalin).

U69593 is ((5a, 7a, 8b)-(+)-N-methyl-N-(7-[1-pyrrolidinyl]-1-oxasipro[4,5]dec-8-yl)-benzeneacetamide).

SNC-80 is (+)-4-[(αR)-α((2S,5R)-4-allyl-2,5-dimethyl-1-piperazinyl)-3-methoxybenzyl]-N,N-diethylbenzamide. nor BNI is nor-binaltorphimine.

CTOP is 1,2-Dithia-5,8,11,14,17-pentaazacycloeicosane, cyclic peptide derivative DPDPE is [D-en2,D-Pen5]enkephalin).

[3H]-DAMGO, [3H]-U69593, norBNI, and CTOP are all commercially available from DuPont, Amersham International, RBI and DuPont, Amersham International, RBI and DuPont respectively.

[3H]-SNC80 was prepared by Amersham International.

Opioid (mu and kappa) receptor binding assays can be performed in guinea-pig brain membrane preparations. Binding assays can be carried out at 25° C. for 60 minutes in 50 mM Tris (pH 7.4) buffer. [$^3$H]-DAMGO(2 nM) and [$^3$H]-U-69,593 (2 nM) can be used to label mu and kappa receptor binding sites, respectively. The protein concentration can be approximately 200 μg/well. Non-specific binding can be defined with 10 μM naloxone.

Delta receptor binding assays can be performed in a stable line of CHO cells expressing the human delta receptor. The binding assay can be carried out at 25° C. for 120 minutes in 50 mM Tris (pH 7.4) buffer. [$^3$H]-SNC-80 can be used to label delta receptor binding sites. The protein concentration can be approximately 12.5 μg/well. Non-specific binding can be defined with 10 μM naltrexone.

The binding reaction can be terminated by rapid filtration through glass fibre filters, and the samples can be washed with ice-cold 50 mM Tris buffer (pH 7.4).

Agonist activity at the delta, mu and kappa opioid receptors can be determined as follows.

Opioid (delta, mu and kappa) activity is studied, as described below, in two isolated tissues, the mouse deferens (MVD)(δ) and the guinea-pig myentric plexus with attached longitudinal muscle (GPMP) (μ and k).

MVD (DC1 strain, Charles River, 25–35 g) are suspended in 15 ml organ baths containing Mg$^{++}$ free Krebs' buffer of the following composition (mM): NaCl, 119; KCl, 4.7; NaHCO$_3$, 25; KH$_2$PO$_4$, 1.2; CaCl$_2$, 2,5 and glucose, 11. The buffer is gassed with 95% 0$_2$ a 5% CO$_2$. The tissues are suspended between platinum electrodes, attached to an isometric transducer with 500 mg tension and stimulated with 0.03 Hz pulses of 1-msec pulse-width at supramaximal voltage. IC$_{50}$ values are determined by the regression analysis of concentration-response curves for inhibition of electrically-induced contractions in the presence of 300 nM of the mu-selective antagonist CTOP. This test is a measure of δ agonism.

Guinea-pig (Porcellus strain, male, 450–500 g, Dunkin Hartley) myentric plexus with attached longitudinal muscle segments are suspended with 1 g of tension in Krebs' buffer and stimulated with 0.1 Hz pulses of 1-msec pulse-width at supramaximal voltage. Mu functional activity is determined in the presence of 10 nM nor-BNI with 1 μM of the mu selective agonist, DAMGO, added to the bath at the end of the experiment to define a maximal response. This test is a measure of mu agonism.

Kappa functional activity is determined in the presence of and 1 μM CTOP with 1 μM of the kappa selective agonist U-69,593 added at the end of the experiment to define a maximal response. All inhibitions of twitch height for test compounds are expressed as a percentage of the inhibition obtained with the standard agonist and the corresponding IC$_{50}$ values determined.

The following procedure can be used to determine the activity of the therapeutic agents of this invention as agonists and as antagonists of delta opioid receptors.

Cell Culture: Chinese hamster ovary cells expressing the human delta opioid receptor are passaged twice weekly in Hamis F-12 media with L-glutamine containing 10% fetal bovine serum and 450 μg/mL hygromycin. Cells are prepared for assays 3 days prior to the experiment. 15 mL of 0.05% trypsin/EDTA is added to a confluent triple flask, swirled and decanted to rinse. 15 mL of 0.05% trypsin/EDTA is again added, and the flask is placed into a 37C incubator for 2 minutes. Cells are removed from the flask by banking, and supernatant poured off into a 50 mL tube. 30 mL of media is then added to the flask to stop the action of the trypsin, and then decanted into the 50 mL tube. Tube is then centrifuged for 5 minutes at 1000 rpm, media decanted, and the pellet resuspended into 10 mL of media. Viability of the cells is assessed using trypan blue, the cells counted and plated out into 96 well poly-D-lysine coated plates at a density of 7,500 cells/well.

Antagonist Test Plate: Cells plated 3 days prior to assay are rinsed twice with PBS. The plates are placed into a 37C water bath. 50 μL of assay buffer (PBS, dextrose 1 mg/mL, 5 mM MgC12, 30 mM HEPES, 66.7 μg/mL of IBMX) is then added to designated wells. Fifty microliters of appropriate drug is then added to designated wells, and timed for 1 minute. Fifty microliters of 10 μM forskolin+0.4 nM DPDPE (final assay concentration is 5 μM forskolin, 0.2 nM DPDPE) is then added to appropriate wells, and timed for 15 minutes. The reaction is stopped by the addition of 10 μL of 6N perchloric acid to all wells. To neutralize, 13 μL of 5N KOH is added to all wells, and to stabilize 12 μL of 2M Tris, pH 7.4 is added to all wells. Mix by shaking on an orbital shaker for 10 minutes, and centrifuge at setting 7 for 10 minutes. Aliquot into 3H plate.

Agonist Test Plate: Cells plated 3 days prior to assay are rinsed twice with PBS. The plates are placed into a 37° C. water bath. Fifty microliters of assay buffer (PBS, dextrose 1 mg/mL, 5 mM MgCl$_2$, 30 mM HEPES, 66.7 μg/mL of IBMX) is then added to designated wells. Fifty microliters of appropriate drug+10 μM forskolin (final assay concentration is 5 μM forskolin) is then added to all wells, and timed for 15 minutes. The reaction is then stopped by the addition of 10 μL of 6N perchloric acid to all wells. To neutralize, 13 μL of 5N KOH is added to all wells, and to stabilize 12 μL of 2M Tris, pH 7.4 is added to all wells. Mix by shaking on an orbital shaker for 10 minutes, and centrifuge at setting 7 for 10 minutes. Aliquot into 3H plate.

Both test plates are placed into an Amersham 3H CAMP binding kit overnight, and harvested onto GF/B filters previously soaked in 0.5% PEI with a Skatron using 50 mM Tris HCl pH 7.4 at 4° C. Filtermats can be air-dried overnight then place in bags with 20 ml Betaplate scintillation cocktail and counted on a Betaplate counter for 60 sec per sample. Data can be analyzed using Excel.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Altemabvely, the active ingredient may be in powder form for reconstitution with a suitable vehicle, e.a, sterile pyrogen-free water, before use.

The active compounds of the invention may also be formulated in rectal compositions such as suppositories or retention enemas, e.g, containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressuried container or nebulizer may contain a solution or suspension of the active compound. Capsules and cartridges (made, for example, from gelatin) for use in an inhaler or insufator may be formulated containing a powder mix of a compound of the invention and a suitable powder base such as lactose or starch.

In general, a therapeutically effective daily oral or intravenous dose of the compounds of formula (I) and their salts is likely to range from 0.001 to 50 mg/kg body weight of the subject to be treated, preferably 0.1 to 20 mg/kg. The compounds of the formula (I) and their salts may also be administered by intravenous infusion, at a dose which is likely to range from 0.001–10 mg/kg/hr.

Tables or capsules of the compounds may be administered singly or two or more at a time as appropriate. It is also possible to administer the compounds in sustained release formulations.

The physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

Alternatively, the compounds of the formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilizers and preservatives as may be required.

The following Examples illustrate the preparation of the compounds of the present invention. Commercial reagents were utilized without further purification. All NMR data were recorded at 250, 300 or 400 MHz in deuterochloroform unless otherwise specified and are reported in parts per million ($\delta$) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C.

EXAMPLE 1

2-[1-Benzyl-4-(3-Methoxy-phenyl)-piperidin-4-yl]-pyrimidine-5-carboxylic Acid Diethylamide A. 2-Allyl-2-(3-methoxy-phenyl)-pent-4-enenitrile To a stirring solution of (3-Methoxy-phenyl)-acetonitrile (25.0 g (grams), 169 mmol) in 200 mL of 50% sodium hydroxide (NaOH) at room temperature was added hexadecyltributylphosphonium bromide (4.31 g, 8.51 mmol) and allyl bromide (103 g, 849 mmol). The mixture was refluxed for 2 hours, cooled to room temperature and extracted with ethyl acetate (EtOAc) (4×120 mL). The combined organic layers were dried and oncentrated. The crude material was purified by flash chromatography with 20% tOAc/hexanes to afford 38.1 g (98% yield) of the desired nitrile. $^1$HNMR (400 MHz, CDCl$_3$) $\delta$ 7.28 (t, 1H), 6.98–6.93 (comp, 2H), 6.81 (d, 1H), 5.69–5.58 (comp, 2H), 5.15–5.11 (comp, 4H), 3.79 (s, 3H), 2.67–2.65 (comp, 4H); MS (M+1)

B. 2-Allyl-2-(3-methoxy-phenyl)-pent-4-enamidine

To a suspension of NH$_4$Cl (13.5 9, 251 mmol) in 170 mL toluene at 0° C. was added a 2.0 M solution of AlMe$_3$ (126 mL, 251 mmol) dropwise. The mixture was warmed to room temperature and stirred for 4 hours. 2-Allyl-2-(3-methoxy-phenyl)-pent-4-enenitrile (38.1 g, 167 mmol) in 30 mL toluene was added and the mixture was heated to 80° C. for 48 hours. The mixture was cooled to room temperature and poured into a stirring suspension of silica gel (50 g) in 150 mL chloroform (CHCl$_3$). After stirring for 30 minutes, the suspension was filtered and the silica gel was washed with methanol (MeOH). The remaining solution was concentrated to an oil and 80 mL acetone was added. The resulting suspension was filtered, the solution was concentrated and the resulting residue was dissolved in 1N hydrochloric acid (HCl)/MeOH (200 mL). The solution was concentrated, 200 mL ethyl ether (Et$_2$O) was added and the resulting precipitate was removed by filtration and dried yielding 22.4 9 (49% yield) of the desired product. $^1$HNMR (400 MHz, CD$_3$OD) δ 8.73, 8.58 (2 brs, 3H, N$\underline{H}$), 7.34 (t, 1H), 6.93–6.91 (comp, 2H), 6.90–6.83 (comp, 1H), 5.56–5.44 (comp, 2H), 5.18–5.14 (comp, 4H), 3.79 (s, 3H), 2.82–2.79 (comp, 4H); MS (M+1) 245.3.

C. 2-[1-Allyl-1-(3-methoxy-phenyl)-but-3-enyl]-pyrimidine-5-carbaldehyde

Ethanol (500 mL) was added dropwise to sodium hydride (NaH) (8.62 9, 215 mmol) at 0° C. and the resulting mixture was stirred for 20 minutes. 2-Allyl-2-(3-methoxy-phenyl)-pent-4-enamidine (20.1 g, 71.8 mmol) and 2-dimethylaminomethylene-1,3-bis(dimethylimmonio) propane bisperchlorate (27.4 g, 71.8 mmol) were added in one portion and the resulting mixture was heated to reflux for 24 hours. The mixture was cooled to room temperature and concentrated under reduced pressure. The resulting residue was taken up in 300 mL tetrahydrofuran (THF), 350 mL 1N HCl was added slowly and the solution stirred for 1 hour at room temperature. The mixture was basified with NaOH (pH=8–9) and extracted with CH$_2$Cl$_2$ (3×250 mL). The combined organic layers were dried and concentrated. The resulting crude material was purified by flash chromatography with 20% EtOAc/hexanes to afford 17.9 g (81%) of the desired aldehyde. $^1$HNMR (400 MHz, CDCl$_3$) δ 10.1 (s, 1H), 9.09 (s, 2H), 7.19 (t, 1H), 6.74–6.70 (comp, 3H), 5.47–5.37 (comp, 2H), 5.02–4.92 (comp, 4H), 3.73 (s, 3H), 3.20–3.05 (comp, 4H); MS (M+1) 309.3.

D. 2-[1-Allyl-1-(3-methoxy-phenyl)-but-3-enyl]-pyrimidine-5-carboxylic Acid Methyl Ester To a vigorously stirring solution of 2-[-Allyl-1-(3-methoxy-phenyl)-but-3-enyl]-pyrimidine-5-carbaldehyde (17.4 g, 56.4 mmol) in 180 mL 2-methyl-2-butene and 180 mL of 2-methyl-2-propanol at 0° C. was added a 1.25 M solution of potassium phosphate (KH$_2$PO$_4$) (271 mL, 338 mmol) and sodium chlorite (NaClO$_2$) (25.5 g, 282 mmol). The mixture was stirred at room temperature for 1 hour, acidified with HCl (pH=3–4) and extracted with EtOAc (3×300 mL). The combined organic layers were dried over MgSO$_4$, filtered and concentrated to yield 19.1 grams (g) of the corresponding carboxylic acid.

To a stirring solution of the crude acid (17.0 g, 52.5 mmol) prepared above in 400 mL methylene chloride (CH$_2$Cl$_2$) at room temperature was added 1,1'-carbonyl diimidazole (11.1 g, 68.2 mmol) in one portion. After 2 hours, MeOH (53 mL, 262 mmol) was added and the resulting mixture stirred at room temperature for 1.5 hours. The solution was concentrated and the resulting crude material was purified by flash chromatography with 40% EtOAc/hexanes to afford 15.0 g (84%) of the desired methyl ester; $^1$HNMR (400 MHz, CDCl$_3$) δ 9.19 (s, 2H), 7.16 (t, 1H), 6.73–6.68 (comp, 3H), 5.46–5.36 (comp, 2H), 5.01–4.91 (comp, 4H), 3.92 (s, 3H), 3.72 (s, 3H), 3.71–3.04 (comp, 4H); MS (M+1) 339.3.

E. 2-[1-Benzyl-4-(3-methoxy-phenyl)-piperidin-4-yl-pyrimidine-5-carboxylic Acid Methyl Ester To a stirring solution of 2-[1-Allyl-1-(3-methoxy-phenyl)-but-3-enyl]-pyrimidine-5-carboxylic acid methyl ester (14.0 g, 41.4 mmol) in 200 mL acetone/water (9:1) at room temperature was added N-methylmorpholine-N-oxide (12.3 g, 91.2 mmol) followed by a 2.5% solution of osmium tetraoxide (OsO$_4$) (5.14 mL, 0.41 mmol). After stirring 24 hours, florisil (14 g), sodium bisulfite (NaHSO$_3$) (9.4 g) and water (60 mL) were added and the resulting suspension was stirred at room temperature for 1 hour. The mixture was filtered over a Celite pad and the pad washed several times with acetone. The resulting solution was concentrated to yield the crude tetra-ol.

To a stirring solution of the tetra-ol prepared above in EtOH (400 mL) at room temperature was added sodium periodate (NaIO$_4$) (40.0 g, 186 mmol) in water (150 mL). The mixture was stirred for 24 hours, filtered over Celite and extracted with ethyl acetate (EtOAc) (3×200 mL). The combined organic layers were dried and concentrated to yield the crude di-aldehyde.

To a stirring solution of the di-aldehyde prepared above in 200 mL CH$_2$Cl$_2$ at room temperature was added benzyl amine (6.57 g, 61.4 mmol), AcOH (3.7 g, 61.4 mmol) and sodium triacetoxy borohydride (NaBH(OAc)$_3$) (26.0 g, 123 mmol). After 24 hours, sodium bicarbonate (NaHCO$_3$) (200 mL) was added, the layers were separated, the aqueous layer extracted with CH$_2$Cl$_2$ (3×150 mL) and the combined organic layers were dried and concentrated. The crude material was purified by flash chromatography with 75% EtOAc/hexanes to afford 5.5 g (35%) of the desired amine. $^1$HNMR (400 MHz, CDCl$_3$) δ 9.19 (s, 2H), 7.29–7.23 (comp, 5H), 7.17 (t, 1H), 6.97–6.93 (comp, 2H), 6.69–6.66 (comp, 1), 3.93 (s, 3H), 3.73 (s, 3H), 3.41 (s, 2H), 3.12–3.03 (comp, 2H), 2.99–2.79 (comp, 2H), 2.44–2.37 (comp, 2H), 2.12–2.03 (comp, 2H); MS (M+1) 418.2.

F. 2-[1-Benzyl-4-(3-methoxy-phenyl)-piperidin-4-yl]-pyrimidine-5-carboxylic Acid Diethylamide To a stirring suspension of diethyl amine hydrochloride (986 mg, 9.01 mmol) in 1,2-dicloroethane (25 mL) at 0° C. was added a 2.0 M solution of AlMe$_3$ (4.5 mL, 9.01 mmol) dropwise. The resulting mixture stirred at room temperature for 1 hour. (2-[1-Benzyl-4-(3-methoxy-phenyl)-piperidin-4-yl]-pyrimidine-5-carboxylic acid methyl ester (750 mg, 1.80 mmol) was added in one portion and the mixture was heated to 85° C. for 16 hours. The reaction was slowly poured into a saturated solution of Rochelle salts (50 mL) and diluted with CH$_2$Cl$_2$ (50 mL). The layers were separated, the aqueous layer was extracted with CH$_2$Cl$_2$ (3×30 mL) and the combined organic layers were dried and concentrated. The crude material was filtered through a plug of silica gel with 5% MeOH/CHCl$_3$, and the resulting solution was concentrated to yield 815 mg (99% yield) of the desired amide. $^1$HNMR (400 MHz, CDCl$_3$) δ 8.72 (s, 2H), 7.29–7.14 (comp, 6H), 6.97–6.95 (comp, 2H), 6.68–6.66 (comp, 1H), 3.73 (s, 3H), 3.54–3.52 (comp, 2H), 3.39 (s, 2H), 3.27–3.25 (comp, 2H), 2.98–2.95 (comp, 2H), 2.77–2.74 (comp, 2H), 2.34–2.31 (comp, 2H), 2.16–2.02 (comp, 2H), 1.26–1.17 (comp, 6H); MS (M+1) 459.2.

Alternatively, the amides were produced from the corresponding carboxylic acid by reaction with CDI and the corresponding amines.

(2-[1-Benzyl-4-(3-methoxy-phenyl)-piperidin-4-yl]-pyrimidine-5-carboxylic acid methyl ester (1 equivalent) was dissolved in water/MeOH (3:1) and LiOH (5 equivalents) was added in one portion. After stirring 24 hours at room temperature, the mixture was acidified with HCl, and extracted with EtOAc (3×). The combined organic layers were dried and concentrated to yield the corresponding carboxylic acid in yields ranging from 80–95%.

To a stirring solution of the carboxylic acid (1 equivalent) in $CH_2Cl_2$ (0.5 M) at room temperature was added 1,1'-carbonyldiimidazole (1.3 equivalents) in one portion. After stirring 1.5 hours at room temperature, $Et_2NH$ (2 equivalents) was added and the reaction mixture stirred 1–3 hours. The reaction mixture was poured into $NaHCO_3$ and $CH_2Cl_2$, the aqueous layer was extracted with $CH_2Cl_2$ (3×) and the combined organic layers were dried and concentrated. The crude material was purified by flash chromatography to afford the desired amides in yields ranging from 75–95%.

The following compounds were made using the procedures set forth above in Example 1, starting with a compound analogous to the title compound of example 1A wherein $R^3$ is fluoro or methoxy, and adding the appropriate amine reactant in the procedure of Example 1E and/or Example 1F.

2-[4-(3-Methoxy-phenyl)-1-(2-methyl-pentyl)-piperidin-4-yl]-pyrimidine-5-carboxylic acid dimethylamide. $^1$HNMR (400 MHz, $CDCl_3$) δ 8.75 (2, 2H), 7.16 (t, 1H), 3.74 (s, 3H), 3.06 (s, 6H), 0.83–0.98 (comp, 6H); MS (M+1) 425.4.

2-[4-(3-Methoxy-phenyl)-1-(2-methyl-pentyl)-piperidin-4-yl]-pyrimidine-5-carboxylic acid ethyl-methyl-amide. $^1$HNMR (400 MHz, $CDCl_3$) δ 8.72 (2, 2H), 7.16 (t, 1H), 3.73 (s, 3H), 3.05 (s, 3H), 3.57–3.55 (comp, 1H), 3.29–3.27 (comp, 1H), 0.82–0.95 (comp, 6H); MS (M+1) 439.4.

{2-[4-(3-Methoxy-phenyl)-1-(2-methyl-pentyl)-piperidin-4-yl]-pyrimidin-5-yl}-(4-methyl-piperazin-1-yl)-methanone. $^1$HNMR (400 MHz, $CDCl_3$) δ 8.73 (2, 2H), 7.16 (t, 1H), 3.62–3.59 (comp, 2H), 3.48–3.43 (comp, 2H), 0.82–0.91 (comp, 6H); MS (M+1) 480.4

EXAMPLE 2

Deprotection of Methyl Aryl Ethers

To a stirring solution of the methyl ether (1 equivalent) and tetrabutylammonium iodide (1.5 equivalents) in $CH_2Cl_2$ (0.3 M) at −78° C. was added a 1.0 M solution of $BCl_3$ (3–7 equivalents) dropwise. The reaction mixture was warmed to room temperature and stirred 1–3 hours. The reaction mixture was quenched by slow addition of water and was brought to pH 8 with $NaHCO_3$. The aqueous layer was extracted with $CH_2Cl_2$, and the combined organic layers were dried and concentrated. The resulting crude material was purified by flash chromatography to afford the desired phenols in yields ranging from 65–91%.

Alternatively, the methyl ethers were deprotected with sodium hydride and ethane thiol in DMF as follows:

To a suspension of NaH (10 equivalents) in DMF (0.2M) at room temperature was added ethane thiol (10 equivalents) dropwise. The mixture was stirred for 5 minutes. To the reaction mixture was added a solution of the methyl ether (1 equivalent) in DMF (0.2M). The mixture was heated to 120° C. for 10–16 hours. The reaction was cooled to room temperature and was quenched with water. The mixture was diluted with diethyl ether and the organic layer was washed with brine. The organic phase was dried ($MgSO_4$) and concentrated. Purification by flash chromatography afforded the desired phenols in yields ranging from 60–95%.

The following compounds were made using the procedure of Example 2.

2-[1-(5-Fluoro-pyrimidin-2-yl)-4-(3-hydroxy-phenyl)-piperidin-4-yl]-pyrimidine-5-carboxylic acid diethylamide. $^1$HNMR (400 MHz, $CDCl_3$) δ 8.76 (s, 2H), 8.16 (s, 2H), 7.10 (t, 1H), 5.98 (br s, 1H), 4.31–4.14 (comp, 2H), 1.26–1.18 (comp, 6H); MS (M+1) 451.2

2[-4-(3-Hydroxy-phenyl)-1-(4-trifluoromethyl-pyrimidin-2-yl)-piperidin-4-yl]-pyrimidine-5-carboxylic acid diethylamide. $^1$HNMR (400 MHz, $CDCl_3$) δ 8.75 (s, 2H), 8.44 (d, 1H), 7.11 (t, 1H), 6.68 (d, 1H), 6.62–6.60 (comp, 1H), 4.45–4.39 (comp, 2H), 1.26–1.18 (comp, 6H); MS (M+1) 501.2.

2-[4-(3-Hydroxy-phenyl)-1-pyrimidin-2-yl-piperidin-4-yl]-pyrimidine-5-carboxylic acid diethylamide. $^1$HNMR (400 MHz, $CDCl_3$) δ 8.75 (s, 2H), 8.29–8.27 (comp, 2H), 7.09 (t, 1H), 4.40–4.37 (comp, 2H), 1.26–1.17 (comp, 6H); MS (M+1) 433.2.

2-[4-(3-Hydroxy-phenyl)-1-pyrazin-2-yl-piperidin-4-yl]-pyrimidine-5-carboxylic acid diethylamide. $^1$HNMR (400 MHz, $CDCl_3$) δ 8.75 (s, 2H), 8.11 (br s, 2H), 7.76 (br s, 1H), 7.13 (t, 1H), 4.13–4.04 (comp, 2H), 1.26–1.18 (comp, 6H); MS (M+1) 433.2.

2-[1-(3,6-Dimethyl-pyrazin-2-yl)-4-(3-hydroxy-phenyl)-piperidin-4-yl]-pyrimidine-5-carboxylic acid diethylamide. $^1$HNMR (400 MHz, $CDCl_3$) δ 8.73 (s, 2H), 7.83 (s, 1H), 7.12 (t, 1H), 2.50 (s, 3H), 2.36 (s, 3H), 1.26–1.18 (comp, 6H); MS (M+1) 461.4.

2-[4-(3-Hydroxy-phenyl)-3,4,5,6-tetrahydro-2H-[1,2'] bipyridinyl-4-yl]-pyrimidine-5-carboxylic acid diethylamide. $^1$HNMR (400 MHz, $CDCl_3$) δ 8.73 (s, 2H), 8.15–8.13 (comp, 1H), 7.12 (t, 1H), 7.46–7.42 (comp, 1H), 4.08–3.97 (comp, 2H), 1.27–1.17 (comp, 6H); MS (M+1) 432.3.

EXAMPLE 3

2-[4-(3-Hydroxy-phenyl)-piperidin-4-yl]-pyrimidine-5-carboxylic Acid Diethylamide To a stirring solution of 2-[1-Benzyl-4-(3-hydroxy-phenyl)-piperidin-4-yl]-pyrimidine-5-carboxylic acid diethylamide (105 mg, 0.24 mmol) in 5 mL 1,2-dichloroethane at room temperature was added potassium carbonate ($K_2CO_3$) (331 mg, 2.4 mmol) and 1-chloroethyl chloroformate (0.16 mL, 1.44 mmol). The mixture was refluxed for 24 hours, cooled to room temperature, filtered and concentrated. The resulting residue was taken up in 15 mL MeOH and refluxed for 24 hours. The mixture was cooled to room temperature and concentrated under reduced pressure to yield 86 mg (91%) of the desired amine. $^1$HNMR (400 MHz, $CD_3OD$) δ 8.78 (s, 2H), 7.04 (t, 1H), 6.82–4.79 (comp, 2H), 6.54 (d, 1H), 3.55–3.32 (comp, 2H), 3.33–3.29 (comp, 2H), 2.99–2.93 (comp, 4H), 2.68 (t, 2H), 2.21 (t, 2H), 1.24–1.15 (comp, 6H); MS (M+1) 355.3

EXAMPLE 4

General Procedure for the Reductive Alkylations of 2-[4-(3-Hydroxy, Fluoro or Methoxy-phenyl)-piperidin-4-yl]-pyrimidine-5-carboxylic Acid Diethylamide To a stirring solution of 2-[4-(3-Hydroxy-phenyl)-piperidin-4-yl]-pyrimidine-5-carboxylic acid diethylamide in $CH_2Cl_2$ (0.3 M) at room temperature was added the aldehyde (1.3 equivalents), acetic acid (AcOH) (1.3 equivalents) and $NaBH(OAc)_3$ (1.5 equivalents). The mixture was stirred at room temperature for up to 24 hours. The reaction was quenched by the addition of saturated NaHCO$_3$ and extracted with CH$_2$Cl$_2$ (3×). The combined organic layers were dried and concentrated. The resulting crude material was purified by flash chromatography to afford the desired tertiary amines in 50–90% yield.

The following compounds were made using the above procedure of Example 4, starting with a diarylsubstituted piperidine wherein R$^3$ is hydroxy, fluoro or methoxy and R$^2$ is the appropriate amide group.

2-[4-(3-Hydroxy-phenyl)-1-(2-methyl-pentyl)-piperidin-4-yl]-pyrimidine-5-carboxylic acid diethylamide. $^1$HNMR (400 MHz, CDCl$_3$) δ 8.72 (s, 2H), 7.25 (t, 1H), 3.54–3.53 (comp, 2H), 3.28–3.26 (comp, 2H), 2.35–2.15 (comp, 2H), 1.32–1.19 (comp, 10H), 0.99–0.81 (comp, 6H); MS (M+1) 439.3.

2-[1-Benzyl-4-(3-hydroxy-phenyl)-piperidin-4-yl]-pyrimidine-5-carboxylic acid diethylamide. $^1$HNMR (400 MHz, CDCl$_3$) δ 8.68 (s, 2H), 7.33–7.24 (comp, 5H), 7.03 (t, 1), 3.26–3.23 (comp, 2H), 1.23–1.16 (comp, 6H); MS (M+1) 445.0.

2-[1-Butyl-4-(3-hydroxy-phenyl)-piperidin-4-yl]-pyrimidine-5-carboxylic acid diethylamide. $^1$HNMR (400 MHz, CDCl$_3$) δ 8.72 (s, 2H), 7.05 (t, 1H), 3.54–3.26 (comp, 2H), 3.40–3.28 (comp, 2H), 2.35–2.15 (comp, 2H), 0.92–0.79 (comp, 6H); MS (M+1) 411.3

2-[4-(3-Hydroxy-phenyl)-1-pentyl-piperidin-4-yl]-pyrimidine-5-carboxylic acid diethylamide. $^1$HNMR (400 MHz, CDCl$_3$) δ 8.71 (s, 2H), 7.03 (t, 1H), 3.54–3.52 (comp, 2H), 3.28–3.26 (comp, 2H), 0.82 (t, 3H); MS (M+1) 397.2.

2-[4-(3-Hydroxy-phenyl)-1-(1H-imidazol-2-ylmethyl)-piperidin-4-yl]-pyrimidine-5-carboxylic acid diethylamide. $^1$HNMR (400 MHz, CD$_3$OD) δ 8.83 (s, 2H), 7.71 (s, 2H), 7.09 (t, 1H), 1.25–1.16 (comp, 6H); MS (M+1) 435.2.

2-[4-(3-Hydroxy-phenyl)-1-(3,5,5-trimethyl-hexyl)-piperidin-4-yl]-pyrimidine-5-carboxylic acid diethylamide. $^1$HNMR (400 MHz, CDCl$_3$) δ 8.74 (s, 2H), 7.05 (t, 1H), 3.55–3.53 (comp, 2H), 3.29–3.27 (comp, 2H), 0.85–0.81 (comp, 12H); MS (M+1) 481.4.

2-[1-(2-Benzyloxy-propyl)-4-(3-hydroxy-phenyl)-piperidin-4-yl]-pyrimidine-5-carboxylic acid diethylamide. $^1$HNMR (400 MHz, CDCl$_3$) δ 8.69 (s, 2H), 7.05 (t, 1H), 4.49 (q, 2H), 3.53–3.51 (comp, 2H), 3.25–3.23 (comp, 2H), 1.28–1.13 (comp, 9H); MS (M+1) 503.2

2-[1-(2-Ethoxy-propyl)-4-(3-hydroxy-phenyl)-piperidin-4-yl]-pyrimidine-5-carboxylic acid diethylamide. $^1$HNMR (400 MHz, CDCl$_3$) δ 8.72 (s, 2H), 7.05 (t, 1H), 3.35–3.26 (comp, 2H), 1.24–1.09 (comp, 12H); MS (M+1) 441.3.

2-[4-(3-Hydroxy-phenyl)-1-thiophen-2-ylmethyl-piperidin-4-yl]-pyrimidine-5-carboxylic acid diethylamide. $^1$HNMR (400 MHz, CDCl$_3$) δ 8.70 (s, 2H), 7.23–7.03 (comp, 3H), 3.53 (br s, 2H), 3.25 (br s, 2H), 1.22–1.16 (comp, 6H); MS (M+1) 451.4.

2-[1-(2-Benzyloxy-ethyl)-4-(3-hydroxy-phenyl)-piperidin-4-yl]-pyrimidine-5-carboxylic acid diethylamide. $^1$HNMR (400 MHz, CDCl$_3$) δ 8.72 (s, 2H), 7.31–7.22 (comp, 5H), 7.04 (t, 1H), 4.46 (s, 2H), 3.59–3.52 (comp, 4H), 3.26–3.24 (comp, 2H), 6H); MS (M+1) 489.2.

2-[4-(3-Hydroxy-phenyl)-1-(2-phenoxy-ethyl)-piperidin-4-yl]-pyrimidine-5-carboxylic acid diethylamide. $^1$HNMR (400 MHz, CDCl$_3$) δ 8.72 (s, 2H), 7.04 (t, 1H), 4.08 (comp, 2H), 3.53–3.51 (comp, 2H), 3.24–3.22 (comp, 2H), 1.24–1.14 (comp, 6H); MS (M+1) 475.3.

2-[4-(3-Hydroxy-phenyl)-1-(2-propoxy-ethyl)-piperidin-4-yl]-pyrimidine-5-carboxylic acid diethylamide. $^1$HNMR (400 MHz, CDCl$_3$) δ 8.73 (s, 2H), 7.05 (t, 1H), 3.56–3.53 (comp, 4H), 3.34–3.22 (comp, 4H), 0.85 (t, 3H); MS (M+1) 441.3.

2-[1-Furan-2-ylmethyl-4-(3-hydroxy-phenyl)-piperidin-4-yl]-pyrimidine-5-carboxylic acid diethylamide. $^1$HNMR (400 MHz, CDCl$_3$) δ 8.72 (s, 2H), 7.31 (s, 1H), 7.05 (t, 1H), 6.26 (comp, 1H), 6.15 (d, 1H), 3.53 (br s, 2H), 3.26 (br s, 2H), 1.24–1.17 (comp, 6H); MS (M+1) 435.2.

2-[1-(3-Ethoxy-propyl)-4-(3-hydroxy-phenyl)-piperidin-4-yl]-pyrimidine-5-carboxylic acid diethylamide. $^1$HNMR (400 MHz, CDCl$_3$) δ 8.73 (s, 2H), 7.05 (t, 1H), 3.54–3.53 (comp, 2H), 3.46–3.39 (comp, 4H), 3.29–3.27 (comp, 2H), 1.24–1.11 (comp, 9H); MS (M+1) 441.3.

2-[4-(3-Hydroxy-phenyl)-1-(3-phenoxy-propyl)-piperidin-4-yl]-pyrimidine-5-carboxylic acid diethylamide. $^1$HNMR (400 MHz, CDCl$_3$) δ 8.73 (s, 2H), 7.25–7.20 (comp, 2H), 7.07 (t, 1H), 3.96–3.93 (comp, 2H), 3.53 (br s, 2H), 3.27 (br s, 2H), 1.99–1.18 (comp, 6H); MS (M+1) 489.2.

2-[1-(2-Diethylamino-ethyl)-4-(3-hydroxy-phenyl)-piperidin-4-yl]-pyrimidine-5-carboxylic acid diethylamide. $^1$HNMR (400 MHz, DMSO) δ 8.80 (comp, 2H), 7.03–6.99 (comp, 1H), 3.42–3.40 (comp, 2H), 3.17–3.06 (comp, 2H), 2.82 (br s, 2H), 2.66 (br s, 2H); MS (M+1) 454.4.

2-[1-[4-(2-Dimethylamino-ethoxy)-benzyl]-4-(3-hydroxy-phenyl)-piperidin-4-yl]-pyrimidine-5-carboxylic acid diethylamide. $^1$HNMR (400 MHz, CDCl$_3$) δ 8.68 (s, 2H), 7.23–7.21 (comp, 2H), 6.80–6.77 (comp, 4H), 4.07–4.02 (comp, 2H), 3.53–3.51 (comp, 2H), 3.25–3.23 (comp, 2H), 1.99–1.15 (comp, 6H); MS (M+1) 532.3.

2-[4-(3-Hydroxy-phenyl)-1-(4-propoxy-benzyl)-piperidin-4-yl]-pyrimidine-5-carboxylic acid diethylamide. $^1$HNMR (400 MHz, CDCl$_3$) δ 8.70 (s, 2H), 7.29 (d, 2H), 7.01 (t, 1H), 3.89–3.86 (comp, 2H), 3.55–3.53 (comp, 2H), 1.01 (t, 3H); MS (M+1) 503.3

2-[4-(3-Hydroxy-phenyl)-1-(2-phenyl-cyclopropyl)-piperidin-4-yl]-pyrimidine-5-carboxylic acid diethylamide. $^1$HNMR (400 MHz, CDCl$_3$) δ 8.73 (s, 2H), 7.24–7.01 (comp, 6H), 6.86 (d, 1H), 6.82 (s, 1H), 6.57 (d, 1H), 3.54–3.51 (comp, 2H), 3.27–3.25 (comp, 2H), 0.94–0.86 (comp, 2H); MS (M+1) 471.2.

2-[4-(3-Hydroxy-phenyl)-1-(2-methyl-pentyl)-piperidin-4-yl]-pyrimidine-5-carboxylic acid dimethylamide. $^1$HNMR (400 MHz, CDCl$_3$) δ 8.76 (s, 2H), 7.06 (t, 1H), 6.85–6.82 (comp, 2H), 6.59–6.58 (d, 1H), 3.11 (s, 3H), 3.02 (s, 3H), 0.89–0.83 (comp, 6H); (M+1) 411.3.

(3,4-Dihydro-1H-isoquinolin-2-yl)-{2-[4-(3-hydroxy-phenyl)-1-(2-methyl-pentyl)-piperidin-4-yl]-pyrimidin-5-yl}-methanone. $^1$HNMR (400 MHz, CDCl$_3$) δ 8.79 (2, 2H), 7.26–7.11 (comp, 5H), 3.75 (s, 3H), 3.29–3.27 (comp, 1H), 0.84–0.97 (comp, 6H); MS (M+1), 513.3

{2-[4-(3-Hydroxy-phenyl)-1-(2-methyl-pentyl)-piperidin-4-yl]-pyrimidin-5-yl}-(4-methyl-piperazin-1-yl}-methanone. $^1$HNMR (400 MHz, CD$_3$OD) δ 8.72 (s, 2H), 7.08 (t, 1H), 6.88 (d, 1H), 6.81 (s, 1H), 6.57 (d, 1H), 3.78 (br s, 2H), 3.46 (br s, 2H), 0.86–0.81 (comp, 6H); MS (M+1) 466.3.

2-[4-(3-Hydroxy-phenyl)-1-(2-propoxy-ethyl)-piperidin-4-yl]-pyrimidine-5-carboxylic acid ethyl-methyl-amide. $^1$HNMR (400 MHz, CDCl$_3$) δ 8.75–8.72 (comp, 2H), 7.06 (t, 1H), 6.83–6.80 (comp, 2H), 6.61 (d, 1H), 1.55–1.47 (comp, 2H), 0.85 (t, 3H); MS (M+1) 427.2.

2-[4-(3-Hydroxy-phenyl)-1-(2-phenoxy-ethyl)-piperidin-4-yl]-pyrimidine-5-carboxylic acid ethyl-methyl-amide. $^1$HNMR (400 MHz, CDCl$_3$) δ 8.75–8.73 (comp, 2H), 7.25–7.18 (comp, 2H), 7.05 (t, 1H), 6.59 (d, 1H), 4.11–4.08 (comp, 2H), 1.24–1.15 (comp, 3H); MS (M+1) 461.2.

2-[4-(3-Hydroxy-phenyl)-1-(2-methyl-pentyl)-piperidin-4-yl]-pyrimidine-5-carboxylic acid isopropyl-methyl-amide. $^1$HNMR (400 MHz, CDCl$_3$) δ 8.73–8.70 (comp, 2H), 7.05 (d, 1H), 6.86–4.83 (comp, 2H), 6.61–6.59 (comp, 1H), 2.94 (br s, 3H), 2.36 (br s, 2H), 0.88–0.81 (comp, 6H); MS (M+1) 439.3.

2-[4-(3-Hydroxy-phenyl)-1-(2-methyl-pentyl)-piperidin-4-yl]-pyrimidine-5-carboxylic acid methyl-propyl-amide. $^1$HNMR (400 MHz, CDCl$_3$) δ 8.74 (s, 1H), 8.70 (s, 1H), 7.05 (t, 1H), 6.83–6.77 (comp, 2H), 6.58 (d, 1H), 3.47 (t, 1H), 3.20 (t, 1H); MS (M+1) 439.3.

2-[4-(3-Hydroxy-phenyl)-1-(2-methyl-pentyl)-piperidin-4-yl]-pyrimidine-5-carboxylic acid tert-butyl-methyl-amide. $^1$HNMR (400 MHz, CDCl$_3$) δ 8.74 (s, 2H), 7.04 (t, 1H), 6.81–4.79 (comp, 2H), 6.57 (d, 1H), 2,12 (br s, 2H), 1.48 (s, 9H), 0.89–0.81 (comp, 6H); MS (M+1) 453.3.

2-[4-(3-Hydroxy-phenyl)-1-(2-methyl-pentyl)-piperidin-4-yl]-pyrimidine-5-carboxylic acid diisopropylamide. $^1$HNMR (400 MHz, CDCl$_3$) δ 8.67 (s, 2H), 7.06 (t, 1H), 6.87–4.85 (comp, 2H), 6.60 (d, 1H), 3.82 (br s, 1H), 3.54 (br s, 1H), 0.88–0.81 (comp, 6H); MS (M+1) 467.3.

2-[4-(3-Hydroxy-phenyl)-1-(2-methyl-pentyl)-piperidin-4-yl]-pyrimidine-5-carboxylic acid cyclopropyl-methyl-amide. $^1$HNMR (400 MHz, CDCl$_3$) δ 8.83 (s, 2H), 7.05 (t, 1H), 6.79–6.76 (comp, 2H), 6.57 (d, 1H), 3.09 (br s, 3H), 0.88–0.82 (comp, 6H), (br s, 2H), 0.42 (br s, 2H); MS (M+1) 437.2.

2-[4-(3-Hydroxy-phenyl)-1-(2-methyl-pentyl)-piperidin-4-yl]-pyrimidine-5-carboxylic acid ethyl-methyl-amide. $^1$HNMR (400 MHz, CDCl,) δ 8.74–8.72 (comp, 2H), 7.01 (t, 1H), 6.86 (br s, 1H), 6.76–4.74 (comp, 1H), 6.62 (d, 1H), 0.91 (d, 3H), 0.83 (t, 3H); MS (M+1) 425.2.

2-[1-Benzyl-4-(3-hydroxy-phenyl)-piperidin-4-yl]-pyrimidine-5-carboxylic acid dimethylamide. $^1$HNMR (400 MHz, CDCl$_3$) δ 8.74 (s, 2H), 7.05 (t, 1H), 6.83 (d, 1H), 6.76 (s, 1H), 6.55 (d, 1H), 3.11 (s, 3H), 3.01 (s, 3H); MS (M+1) 417.2.

EXAMPLE 5

Alkylation of 2-[4-(3-Methoxy-phenyl)-piperidine-4-yl]-pyrimidine-5-carboxylic Acid Diethylamide To a stirring solution of 2-[4-(3-Methoxy-phenyl)-piperidin-4-yl]-pyrimidine-5-carboxylic acid diethylamide (1 equivalent) in either dimethylformamide (DMF) or benzene (0.5 M) was added either triethylamine (Et$_3$N) or Na$_2$CO$_3$ (5–10 equivalents) and the alkyl or heteroaryl halide (1–6 equivalents). The reaction mixtures were stirred at 60–120° C. for 2–24 hours. The reaction mixture was quench with NaHCO$_3$ and extracted with CH$_2$Cl$_2$ (3×). The combined organic layers were dried and concentrated. The crude materials were purified by flash chromatography to afford the desired alkylated amines in yields ranging from 35–65%.

The following compounds were made using a procedure analogous to that of Example 5, starting with the appropriate amide group.

2-[1-(5-Fluoro-pyrimidin-2-yl)-4-(3-methoxy-phenyl)-piperidin-4-yl]-pyrimidine-5-carboxylic acid diethylamide. $^1$HNMR (400 MHz, CDCl$_3$) δ 8.73 (s, 2H), 8.16 (s, 2H), 7.19 (t, 1H), 4.38–4.30 (comp, 2H), 3.75 (s, 3H), 1.26–1.17 (comp, 6H); MS (M+1) 465.3.

2-[4-(3-Methoxy-phenyl)-1-pyrimidin-2-yl-piperidin-4-yl]-pyrimidine-5-carboxylic acid diethylamide. $^1$HNMR (400 MHz, CDCl$_3$) δ 8.74 (s, 2H), 8.27–8.25 (comp, 2H), 7.18 (t, 1H), 4.44–4.05 (comp, 2H), 3.74 (s, 3H), 1.25–1.17 (comp, 6H); MS (M+1) 447.3

2-[4-(3-Methoxy-phenyl)-1-(4-trifluoromethyl-pyrimidin-2-yl)-piperidin-4-yl]-pyrimidine-5-carboxylic acid diethylamide. $^1$HNMR (400 MHz, CDCl$_3$) δ 8.74 (s, 2H), 8.44 (d, 2H), 7.17 (t, 1H), 4.48–4.42 (comp, 2H), 3.74 (s, 3H), 1.26–1.17 (comp, 6H); MS (M+1) 515.4.

2-[4-(3-Methoxy-phenyl)-1-pyrazin-2-yl-piperidin-4-yl]-pyrimidine-5-carboxylic acid diethylamide. $^1$HNMR (400 MHz, CDCl$_3$) δ 8.72 (s, 2H), 8.11 (s, 1H), 7.99 (d, 1H), 7.74 (d, 1H), 7.17 (t, 1H), 4.08–4.01 (comp, 2H), 3.72 (s, 3H), 1.23–1.15 (comp, 6H); MS (M+1) 447.4.

2-[4-(3-Methoxy-phenyl)-3,4,5,6-tetrahydro-2H-[1,2'] bipyridinyl-4-yl]-pyrimidine-5-carboxylic acid diethylamide. $^1$HNMR (400 MHz, CDCl$_3$) δ 8.73 (s, 2H), 8.16–8.14 (comp, 1H), 7.44–7.40 (comp, 1H), 7.18 (t, 1H), 4.11–3.99 (comp, 2H), 3.74 (s, 3H), 1.25–1.17 (comp, 6H); MS (M+1) 446.3.

EXAMPLE 6

Trifluoro-methanesulfonic Acid 3-[-4-(5-Diethylcarbomoyl-pyrimidin-2-yl)-1-(2-mehtyl-pentyl)-piperidin-4-yl]-phenyl Ester To a stirring solution of 2-[4-(3-Hydroxy-phenyl)-1-(2-methyl-pentyl)-piperidin-4-yl]-pyrimidine-5-carboxylic acid diethylamide (200 mg, 0.46 mmol) in 4 mL CH$_2$Cl$_2$ at 0° C. was added 4-dimethylamino pyridine (3.0 mg, 0.023 mmol), pyridine (0.08 mL, 0.92 mmol) and triflic anhydride (0.11 mL, 0.68 mmol). After stirring 1 hour at 0° C., the reaction mixture was quenched with cold NaHCO$_3$ and extracted with CH$_2$Cl$_2$. The combined organic layers were dried and concentrated. Purification of the crude material by flash chromatography afforded 260 mg (99%) of the desired triflate. $^1$HNMR (400 MHz, CDCl$_3$) δ 8.75–8.72 (comp, 2H), 7.46–7.05 (comp, 4H), 3.54 (br s, 2H), 3.25 (br s, 2H), 3.05 (br s, 2H), 2.87 (br s, 2H), 2.36–2.18 (comp, 4H), 1.66 (br s, 1H), 1.45–1.15 (comp, 10H), 0.89–0.87 (comp, 6H); MS (M+1) 571.3.

EXAMPLE 7

2-[4-(3-Cyano-phenyl)-1-(2-mehtyl-pentyl)-piperidin-4-yl]-pyrimidine-5-carboxylic Acid Diethylamide A stirring solution of Trifluoro-methanesulfonic acid 3-[4-(5-diethylcarbamoyl-pyrimidin-2-yl)-1-(2-methyl-pentyl)-piperidin-4-yl]-phenyl ester (260 mg, 0.46 mmol), zinc cyanide (Zn(CN)$_2$) (81 mg, 0.69 mmol) and tetrakistriphenylphosphine palladium (0) (266 mg, 0.23 mmol) in 8 mL DMF was cooled to −78° C. and de-oxygenated via a freeze-thaw process. The reaction mixture was heated to 80° C. for 1.5 hours, cooled to room temperature and filtered. The resulting solution was partitioned between EtOAc and water, the layers were separated and the aqueous layer was extracted with EtOAc (3×15 mL). The combined organic layers were dried and concentrated. The resulting crude material was purified by flash chromatography to afford 173 mg (84%) of the desired nitrile. $^1$HNMR (400 MHz, CDCl$_3$) δ 8.69 (s, 2H), 7.64–7.59 (comp, 1H), 7.41–7.29 (comp, 3H), 3.51–3.49 (comp, 2H), 3.25–3.23 (comp, 2H), 2.97–2.94 (comp, 2H), 2.66 (br s, 2H), 2.27–2.25 (comp, 2H), 2.05–1.90 (comp, 4H), 1.57–1.55 (comp, 1H), 1.31–1.15 (comp, 9H), 0.99–0.95 (comp, 1H), 0.83–0.81 (comp, 6H); MS (M+1) 448.3.

EXAMPLE 8

2-[4-(3-Carbamoyl-phenyl)-1-(2-methyl-pentyl)-piperidin-4-yl]-pyrimidine-5-carboxylic Acid Diethylamine To a stirring solution of 2-[4-(3-cyano-phenyl)-1-(2-methyl-pentyl)-piperidin-4-yl]-pyrimidine-5-carboxylic acid diethylamide (90 mg, 0.20 mmol) in 1.5 mL ethanol (EtOH) at room temperature was added a 3 N solution of sodium carbonate ($Na_2CO_3$) (0.5 mL) and a 30% solution of hydrogen peroxide ($H_2O_2$) (0.14 mL). The reaction mixture was stirred for 24 hours, diluted with 10 mL water and extracted with EtOAc (3×15 mL). The combined organic layers were dried and concentrated. The crude material was purified by flash chromatography to afford 30 mg (35%) of the desired amide. $^1$HNMR (400 MHz, $CDCl_3$) δ 8.71 (s, 2H), 7.89 (s, 1H), 7.58–7.51 (comp, 2H), 7.31 (t, 1H), 6.26 (br s, 1H), 5.88 (br s, 1H), 3.53–3.51 (comp, 2H), 3.26–3.25 (comp, 2H), 3.03–3.00 (comp, 2H), 2.75 (br s, 2H), 2.44–2.42 (comp, 2H), 2.15–2.02 (comp, 4H), 1.63–1.61 (comp, 1H), 1.36–1.16 (comp, 9H), 1.07–0.97 (comp, 1H), 0.87–0.83 (comp, 6H); MS (M+1) 466.3.

The following compounds were made using a procedure analogous to that of Example 8, starting with the appropriate $R^1$ group.

2-[4-(3-Carbamoyl-phenyl)-1-(3,5,5-trimethyl-hexyl)-piperidin-4-yl]-pyrimidine-5-carboxylic acid diethylamide. $^1$HNMR (400 MHz, $CDCl_3$) δ 8.75 (s, 2H), 7.86 (s, 1H), 7.59–7.50 (comp, 2H), 7.32 (t, 1H), 6.22 (br s, 1H), 5.73 (br s, 1H), 3.54–3.52 (comp, 2H), 3.27–3.25 (comp, 2H), 3.08 (br s, 2H), 2.91 (br s, 2H), 2.52–2.26 (comp, 6H), 1.63–1.61 (comp, 1H), 1.54–1.11 (comp, 11H), 0.89–0.82 (comp, 12H); MS (M+1) 508.3.

2-[1-(2-Benzyloxy-ethyl)-4-(3-carbamoyl-phenyl)-piperidin-4-yl]-pyrimidine-5-carboxylic acid diethylamide. $^1$HNMR (400 MHz, $CDCl_3$) δ 8.72 (s, 2H), 7.88 (s, 1H), 7.57–7.47 (comp, 2H), 7.35–7.25 (comp, 6H), 6.26 (br s, 1H), 5.81 (br s, 1H), 4.95 (s, 2H), 3.66–3.64 (comp, 2H), 3.54–3.52 (comp, 2H), 3.26–3.25 (comp, 2H), 3.09–2.97 (comp, 4H), 2.64–2.35 (comp, 6H), 1.23–1.15 (comp, 6H); MS (M+1) 516.3.

2-[4-(3-Carbamoyl-phenyl)-1-(3-cyclohexyl-propyl)-piperidin-4-yl]-pyrimidine-5-carboxylic acid diethylamide. $^1$HNMR (400 MHz, $CDCl_3$) δ 8.73 (s, 2H), 7.89 (s, 1H), 7.58 (d, 1H), 7.47 (d, 1H), 7.32 (t, 1H), 6.33 (br s, 1H), 5.84 (br s, 1H), 3.54–3.52 (comp, 2H), 3.45–3.43 (comp, 2H), 1.23–1.08 (comp, 12H), 0.86–0.81 (comp, 2H); MS (M+1) 506.2.

2-[4-(3-Carbamoyl-phenyl)-1-hexyl-piperidin-4-yl]-pyrimidine-5-carboxylic acid diethylamide. $^1$HNMR (400 MHz, $CDCl_3$) δ 8.72 (s, 2H), 7.88 (s, 1H), 7.57 (d, 1H), 7.49 (d, 1H), 7.30 (t, 1H), 6.33 (br s, 1H), 6.01 (br s, 1H), 3.53–3.51 (comp, 2H), 3.26–3.24 (comp, 2H), 1.29–1.16 (comp, 12H), 0.83 (t, 3H); MS (M+1) 466.2.

2-[4-(3-Carbamoyl-phenyl)-1-(4-fluoro-benzenesulfonyl)-piperidin-4-yl]-pyrimidine-5-carboxylic acid diethylamide. $^1$HNMR (400 MHz, $CDCl_3$) δ 8.62 (s, 2H), 7.78 (s, 1H), 7.71–7.67 (comp, 2H), 7.54 (d, 1H), 7.43 (d, 1H), 7.29 (t, 1H), 7.12 (t, 2H), 6.41 (br s, 1H), 6.20 (br s, 1H), 1.25–1.08 (comp, 6H); MS (M+1) 540.1.

2-[4-(3-Carbamoyl-phenyl)-piperidin-4-yl]-pyrimidine-5-carboxylic acid diethylamide. $^1$HNMR (400 MHz, $CDCl_3$) δ 8.73 (s, 2H), 7.90 (s, 1H), 7.63 (s, 1H), 2.97–2.94 (comp, 2H), 2.55–2.49 (comp, 2H), 1.22–1,17 (comp, 6H); MS (M+1) 382.2.

2-[4-(3-Carbamoyl-phenyl)-1-(4-propoxy-benzyl)-piperidin-4-yl]-pyrimidine-5-carboxylic acid diethylamide. $^1$HNMR (400 MHz, $CDCl_3$) δ 8.72 (s, 2H), 7.88 (s, 1H), 7.57 (d, 1H), 7.44 (d, 1H), 7.29 (t, 1H), 7.17 (d, 2H), 6.80 (d, 2H), 6.39 (br s, 1H), 6.01 (br s, 1H), 3.87 (t, 2H), 3.53–3.51 (comp, 2H), 3.25–3.22 (comp, 2H), 1.23–1.15 (comp, 6H); MS (M+1) 530.1.

2-[4-(3-Carbamoyl-phenyl)-1-(3-ethoxy-propyl)-piperidin-4-yl]-pyrimidine-5-carboxylic acid diethylamide. $^1$HNMR (400 MHz, $CDCl_3$) δ 8.73 (s, 2H), 7.88 (s, 1H), 7.60 (d, 1H), 7.45 (d, 1H), 7.32 (t, 1H), 6.32 (br s, 1H), 5.72 (br s, 1H), 3.54–3.26 (comp, 2H), 1.23–1.14 (comp, 9H); MS (M+1) 468.2.

EXAMPLE 9

2-{1-(2-Methyl-pentyl)-4-[3-(1H-tetrazol-5-yl)-phenyl]-piperidin-4-yl}-pyrimidine-5-carboxylic Acid Diethylamide To a stirring solution of 2-[4-(3-cyano-phenyl)-1-(2-methyl-pentyl)-piperidin-4-yl]-pyrimidine-5-carboxylic acid diethylamide (45 mg, 0.11 mmol) in 4 mL toluene at room temperature was added $Bu_2SnO$ (12 mg, 0.05 mmol) and azidotrimethylsilane (0.09 mL, 0.66 mmol). The reaction mixture was heated to 100° C. for 28 hours and cooled to room temperature. The reaction was quenched with water, neutralized with $NaHCO_3$ and extracted with $CH_2Cl_2$. The combined organic layers were dried and concentrated. The resulting crude material was purified by flash chromatography with 5% $MeOH/CH_2Cl_2$ to afford 25 mg (51%) of the desired tetrazole. $^1$HNMR (400 MHz, $CDCl_3$) δ 8.70 (s, 2H), 8.15 (s, 1H), 7.94 (d, 1H), 7.25–7.13 (comp, 2H), 3.53–3.51 (comp, 4H), 3.25–3.22 (comp, 4H), 2.70 (br s, 6H), 1.93 (br s, 1H), 1.40–1.12 (comp, 10H), 1.01 (d, 3H), 0.81 (t, 3H); MS (M+1) 491.4.

EXAMPLE 10

3-[4-(5-Diethycarbamoyl-pyrimidin-2-yl)-1-(2-mehtyl-pentyl)-piperidin-4-yl]-benzoic Acid Methyl Ester To a solution of trifluoro-methanesulfonic acid 3-[4-(5-diethylcarbamoyl-pyrimidin-2-yl)-1-(2-methyl-pentyl)-piperidin-4-yl]-phenyl ester (345 mg, 0.60 mmol) in MeOH (3 mL) and dimethylsulfoxide (DMSO) (3 mL) in a par pressure bottle, was added lead diacetate (Pd(OAc)$_2$) (96 mg, 0.42 mmol), 1,3-bis(diphenylphosphino)propane (114 mg, 0.28 mmol) and $Et_3N$ (0.67 mL, 4.8 mmol). The reaction mixture was heated to 70° C. under 50 psi carbon monoxide (CO) and shaken for 5 hours. The reaction mixture was cooled to room temperature, filtered through Celite and the Celite pad was washed with EtOAc. The resulting solution was poured into EtOAc and $NaHCO_3$, the layers were separated and the aqueous layer was extracted with EtOAc (3×15 mL). The combined organic layers were dried and concentrated. The crude material was purified by flash chromatography with 75% EtOAc/hexanes to afford 275 mg (96%) of the desired methyl ester. $^1$HNMR (400 MHz, $CDCl_3$) δ 8.70 (s, 2H), 8.07 (s, 1H), 7.80–7.78 (comp, 1H), 7.58–7.56 (comp, 1H), 7.29 (t, 1H), 3.84 (s, 3H), 3.51–3.49 (comp, 2H), 3.24–3.23 (comp, 2H), 2.99–2.94 (comp, 2H), 2.68–2.64 (comp, 2H), 2.36–2.32 (comp, 2H), 2.08–1.91 (comp, 4H), 1.58–1.56 (comp, 1H), 1.33–1.14 (comp, 9H), 1.00–0.93 (comp, 1H), 0.84–0.81 (comp, 6H); MS (M+1) 481.3.

EXAMPLE 11

2-[4-(3-Hydroxymethyl-phenyl)-1-(2-methyl-pentyl)-piperidin-4-yl]-pyrimidine-5-carboxylic Acid Diethylamide To a stirring solution of 2-[4-(3-Hydroxymethyl-phenyl)-1-(2-methyl-pentyl)-piperidin-4-yl]-pyrimidine-5- carboxylic acid diethylamide (600 mg, 1.25 mmol) in 30 mL MeOH/H$_2$O (3:1) at room temperature was added lithium hydroxide (LiOH) (150 mg, 6.25 mmol). The reaction mixture was stirred at room temperature for 24 hours, acidified to pH 2 with 1N HCl and extracted with EtOAc (3×50 mL). The combined organic layers were dried and concentrated to yield the crude carboxylic acid (500 mg).

To a stirring solution of the carboxylic acid (500 mg, 1.23 mmol) prepared above in 20 mL tetrahydrofuran (THF) at 0° C. was added Et$_3$N (0.22 mL, 1.54 mmol) and ethyl chloroformate (0.15 mL, 1.54 mmol). After 1 hour, the reaction mixture was filtered and the resulting solution was reooled to 0° C. and treated with NaBH$_4$ (187 mg, 4.93 mmol) in 5 mL MeOH. The reaction mixture was stirred for 30 minutes, quenched with H$_2$O and extracted with CH$_2$Cl$_2$ (3×50 mL). The combined organic layers were dried and concentrated. The crude material was purified by flash chromatography with 5% MeOH/CH$_2$Cl$_2$ to afford 300 mg (54%) of the desired alcohol. $^1$HNMR (400 MHz, CDCl$_3$) δ 8.71 (s, 2H), 7.23 (s, 1H), 7.29–7.13 (comp, 3H), 4.61–4.51 (comp, 2H), 3.53–3.51 (comp, 2H), 3.27–3.25 (comp, 2H), 2.99–2.97 (comp, 2H), 2.77–2.72 (comp, 2H), 2.40–2.35 (comp, 2H), 2.09–1.95 (comp, 4H), 1.63 (br s, 1H), 1.36–1.04 (comp, 9H), 1.02–0.98 (comp, 1H), 0.88–0.83 (comp, 6H); MS (M+1) 453.4.

EXAMPLE 12

2-[4-[3-4-Hydroxy-ethyl)-phenyl]-1-(2-methyl-pentyl-piperidin-4-yl]-pyrimidine-5-carboxylic Acid Diethylamide To a stirring solution of 2-[4-(3-hydroxymethyl-phenyl)-1-(2-methyl-pentyl)-piperidin-4-yl]-pyrimidine-5-carboxylic acid diethylamide (237 mg, 0.52 mmol) in CH$_2$Cl$_2$ (35 mL) at room temperature was added oven dried 4 angstrom molecular sieves (237 mg), N-methylmorpholine-N-oxide (92 mg, 0.78 mmol) and tetrapropylammonium perruthenate (10 mg, 0.03 mmol). After stirring 15 minutes at room temperature, the reaction mixture was filtered through a Celite pad and the pad was washed several times with CH$_2$Cl$_2$. The resulting solution was concentrated to yield 200 mg (85%) of the desired aldehyde.

To a stirring solution of the aldehyde (60 mg, 0.134 mmol) prepared above in THF at −78° C. was added a 1.0 M solution of methyl magnesium bromide (MeMgBr) (0.27 mL, 0.27 mmol). The reaction was warmed to 0° C. and stirred for 1 hour. The reaction mixture was quenched with NaHCO$_3$, extracted with EtOAc (3×20 mL) and the combined organic layers were dried and concentrated. The crude material was purified by flash chromatography to afford 52 mg (84%) of the desired alcohol. $^1$HNMR (400 MHz, CDCl$_3$) δ 8.71 (s, 2H), 7.37 (s, 1H), 7.29–7.16 (comp, 3H), 4.83–4.81 (comp, 1H), 3.54–3.52 (comp, 2H), 3.38–3.36 (comp, 2H), 3.27–3.26 (comp, 2H), 2.99–2.78 (comp, 2H), 2.43–2.40 (comp, 2H), 2.27–2.09 (comp, 4H), 1.93 (br s, 1H), 1.65–1.56 (comp, 1H), 1.41 (d, 3H), 1.39–1.17 (comp, 10H), 1.06–1.01 (comp, 1H), 0.89–0.83 (comp, 6H); MS (M+1) 467.3.

EXAMPLE 13

2-[1-Benzyl-4-(3-methoxy-phenyl)-piperidin-4-yl]-pyrimidine-5-carboxylic Acid (2-Hydroxy-1,1-dimethyl-ehtyl)-amide To a stirring solution of 2-[1-benzyl-4-(3-methoxy-phenyl)-piperidin-4-yl]-pyrimidine-5-carboxylic acid (375 mg, 0.93 mmol) in 10 mL of CH$_2$Cl$_2$ at room temperature was added oxalyl chloride (0.11 mL, 0.12 mmol) and 0.01 mL DMF. After 1 hour, triethyl amine (0.52 mL, 3.72 mmol) and 2-amino-2-methyl-propan-1-ol (0.13 mL, 1.39 mmol) was added and the resulting mixture stirred for 60 minutes. The reaction was quenched by the addition of NaOH and poured into CH$_2$Cl$_2$. The layers were separated, the aqueous layer was extracted with CH$_2$Cl$_2$ (3×20 mL), and the combined organic layers were dried, filtered and concentrated to yield 350 mg of the desired product. $^1$HNMR (400 MHz, CDCl$_3$) δ 8.98 (s, 2H), 7.28–7.21 (comp, 5H), 7.15 (t, 1H), 6.94–6.91 (comp, 2H), 6.65 (d, 1H), 6.29 (br s, 1H), 3.73 (s, 3H), 3.65 (s, 2H), 3.38 (s, 2H), 2.98–2.96 (comp, 2H), 2.85–2.76 (comp, 2H), 2.33–2.21 (comp, 2H), 2.11–2.08 (comp, 2H), 1.39 (s, 6H); MS (M+1) 475.1.

EXAMPLE 14

2-[1-Benzyl-4-(3-methoxy-phenyl)-piperidin-4-yl]-5-(4,4-dimethyl-4,5-dihydro-oxazol-2-yl)-pyrimidine To a stirring solution of 2-[1-Benzyl-4-(3-methoxy-phenyl)-piperidin-4-yl]-pyrimidine-5-carboxylic acid (2-hydroxy-1,1-dimethyl-ethyl)-amide (350 mg, 0.745 mmol) and triphenylphosphine (290 mg, 1.11 mmol) in tetrahydrofuran (10 mL) at 0° C. was added diethylazodicarboxylate (0.174 mL, 1.11 mmol). The reaction slowly warmed to room temperature and stirred for 3 hours. The crude mixture was concentrated under reduce pressure and purified by flash chromatography with 2% MeOH/CH$_2$Cl$_2$ to afford 175 mg (%) of the desired product. $^1$HNMR (400 MHz, CDCl$_3$) δ 9.12 (s, 2H), 7.33–7.26 (comp, 5H), 7.15 (t, 1H), 6.95–6.91 (comp, 2H), 6.68–4.65 (comp, 1H), 4.09 (s, 2H), 3.72 (s, 3H), 3.42 (br s, 2), 3.04 (br s, 2H), 2.83 (br s, 2H), 2.37 (br s, 2H), 2.03 (br s, 2H), 1.36 (s, 6H); MS (M+1) 457.1

EXAMPLE 15

3-{2-[4-(3-Methoxy-phenyl)-1-(2-methyl-pentyl)-piperidin-4-yl]-pyrimidin-5-yl}-pentan-3-ol To a solution of 2-[4-(3-Methoxy-phenyl)-1-(2-methyl-pentyl)-piperidin-4-yl]-pyrimidine-5-carboxylic acid methyl ester (120 mg, 0.292 mmol) in THF (6 mL) at 0° C. was added ethyl magnesium bromide in t-butylmethyl ether (1 M, 3 mL). The reaction mixture was stirred at room temperature for 18 hours. The reaction was quenched by slow addition of water (5 mL). The aqueous layer was washed with CH$_2$Cl$_2$ (3×10 mL) and the organic extracts were dried (Na$_2$SO$_4$) and concentrated. Purification by flash chromatography with hexanes/EtOAc (3:1) yielded 28 mg of 3-{2-[4-(3-Methoxy-phenyl)-1-(2-methyl-pentyl)-piperidin-4-yl]-pyrimidin-5-yl}-pentan-3-ol. $^1$HNMR (400 MHz, CDCl$_3$) δ 8.68 (s, 2H), 7.15 (t, 1H), 6.96–4.92 (comp, 2H), 6.67–6.64 (m, 1H), 3.73 (s, 3H), 2.94–2.90 (comp, 2H), 2.79–2.69 (comp, 2H), 2.35–2.28 (comp, 2H), 2.07–1.91 (comp, 3H), 1.81 (q, 2H), 1.62–1.59 (comp, 2H), 1.39–1.18 (comp, 4H), 0.89–0.82 (comp, 6H), 0.77 (t, 6H); MS (M+1) 440.3.

The following example was prepared by deprotection of the methyl ether according to the procedures outlined in Example 2.

3-[4-[5-(1-Ethyl-1-hvdroxy-propyl)-pyrimidin-2-yl]-1-(2-methyl-pentyl)-piperidin-4-yl]-phenol. $^1$HNMR (400 MHz, CDCl$_3$) δ 8.68 (s, 2H), 7.07 (t, 1H), 6.76 (d, 1H), 6.64 (s, 1H), 6.57 (d, 1H), 2.27–2.08 (comp, 2H), 1.79 (q, 4H), 0.76 (t, 6H); MS (M+1) 426.4

EXAMPLE 16

2-[4-(3-Amino-phenyl)-1-(2-methyl-pentyl)-piperidin-4-yl]-pyrimidine-5-carboxylic Acid Diethylamide To a stirring solution of 3-[4-(5-Diethylcarbamoyl-pyrimidin-2-yl)-1-(2-methyl-pentyl)-piperidin-4-yl]-benzoic acid (210 mg, 0.45 mmol) in 8 mL Toluene and 2 mL tert-butyl alcohol at room temperature was added triethylamine (0.066 mL, 0.48 mmol) and diphenylphosphoryl azide (0.07 mL, 0.45 mmol). The resulting mixture was heated at 120° C. for 20 hours, cooled to room temperature, washed with water, dried and concentrated. The resulting residue was taken up in EtOH/5N HCl (1:1) and stirred at room temperature for 22 hours. The resulting mixture was basified (pH=9) with NaOH and extracted with EtOAc (3×20 mL). The combined organic layers were dried and concentrated. Purification of the crude material was accomplished by flash chromatography with a solvent gradient of 5% and 10% MeOH/$CH_2Cl_2$ to yield 125 mg of the desired product. $^1$HNMR (400 MHz, $CDCl_3$) δ 8.71 (s, 2H), 7.02 (t, 1H), 6.76 (d, 1H), 6.71 (s, 1H), 6.45 (d, 1H), 3.57–3.52 (comp, 4H), 3.28–3.26 (comp, 2H), 2.93–2.89 (comp, 2H), 2.71 (br s, 2H), 2.33 (br s, 2H), 2.15–1.96 (comp, 4H), 1.61 (br s, 1H), 1.38–1.17 (comp, 10H), 1.03–0.96 (comp, 1H), 0.86–0.83 (comp, 6H); MS (M+1) 438.6.

EXAMPLE 17

2-[4-(3-Methanesulfonylamino-phenyl)-1-(2-methyl-pentyl)-piperidin-4-yl]-pyrimidine-5-carboxylic Acid Diethylamide To a stirring solution of 2-[4-(3-Amino-phenyl)-1-(2-methyl-pentyl)-piperidin-4-yl]-pyrimidine-5-carboxylic acid diethylamide (50 mg, 0.114 mmol) and pyridine (0.01 mL, 0.13 mmol) in 5 mL $CH_2Cl_2$ at −5° C. was added mesyl chloride (0.01 mL, 0.13 mmol). The reaction warmed to room temperature and stirred 48 hours. The mixture was quenched with $NaHCO_3$ and extracted with $CH_2Cl_2$ (3×10 mL). The combined organic layers were dried and concentrated. Purification of the resulting crude material by flash chromatography with 5% MeOH/$CH_2Cl_2$ afforded the desired product (44 mg). $^1$HNMR (400 MHz, $CDCl_3$) δ 8.73 (s, 2H), 7.24–7.17 (comp, 3H), 7.07 (d, 1H), 3.55–3.51 (comp, 2H), 3.33–3.27 (comp, 2H), 3.02–2.94 (comp, 2H), 2.91 (s, 3H), 2.88–2.86 (comp, 2H), 2.45 (br s, 2H), 2.20–2.15 (comp, 4H), 1.68 (br s, 1H), 1.37–1.21 (comp, 10H), 1.05–0.99 (comp, 1H), 0.91–0.83 (comp, 6H); MS (M+1) 516.3.

What is claimed is:

1. A compound of the formula

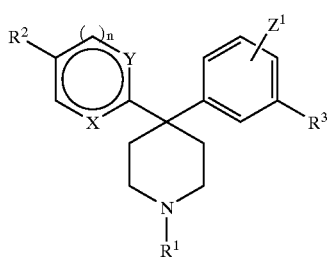

I wherein X and Y are nitrogen with the proviso that the ring containing X and Y must be aromatic;

$()_n$ means $(CH_2)_n$ and n is zero or one;

$R^1$ is hydrogen, $(C_0-C_8)$alkoxy-$(C_0-C_8)$alkyl-, wherein the total number of carbon atoms in said $(C_0-C_8)$alkoxy-$(C_0-C_8)$alkyl- is eight or less, aryl, aryl-$(C_1-C_8)$alkyl-, heteroaryl, heteroaryl-$(C_1-C_8)$alkyl-, heterocyclic, heterocyclic-$(C_1-C_8)$alkyl, $(C_3-C_7)$cycloalkyl-, or $(C_3-C_7)$cycloalkyl-$(C_1-C_8)$alkyl, wherein said aryl and the aryl moiety of said aryl-$(C_1-C_8)$alkyl- are selected, independently, from phenyl and naphthyl, and wherein said heteroaryl and the heteroaryl moiety of said heteroaryl-$(C_1-C_8)$alkyl- are selected, independently, from pyrazinyl, benzofuranyl, quinolyl, isoquinolyl, benzothienyl, isobenzoflryl, pyrazolyl, indolyl, isoindolyl, benzimidazolyl, purinyl, carbazolyl, 1,2,5-thiadiazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, oxazolyl, oxadiazolyl, isoxazolyl, thiazolyl, isothiazolyl, furanyl, pyrrolyl, tetrazolyl, triazolyl, thienyl, imidazolyl, pyridinyl, and pyrimidinyl; and wherein said heterocyclic and the heterocyclic moiety of said heterocyclic-$(C_1-C_8)$alkyl- are selected from saturated or unsaturated nonaromatic monocyclic or bicyclic ring systems, wherein said monocyclic ring systems contain from four to seven ring carbon atoms, from one to three of which may optionally be replaced with O, N or S, and wherein said bicyclic ring systems contain from seven to twelve ring carbon atoms, from one to four of which may optionally be replaced with O, N or S; and wherein any of the aryl, heteroaryl or heterocyclic moieties of $R^1$ may optionally be substituted with from one to three substituents, preferably with one or two substituents, independently selected from halo, $(C_1-C_6)$alkyl optionally substituted with from one to seven fluorine atoms, phenyl, benzyl, hydroxy, acetyl, amino, cyano, nitro, $(C_1-C_6)$alkoxy, $(C_1-C_6)$akylamino and $_2$amino, and wherein any of the alkyl moieties in $R^1$ may optionally be substituted with from one to seven fluorine atoms;

$R^2$ is hydrogen, aryl, halo, heteroaryl, heterocyclic, $SO_2R^4$, $COR^4$, $CONR^5R^6$, $COOR^4$, or $C(OH)R^5R^6$ wherein each of $R^4$, $R^5$ and $R^6$ is defined, independently, as $R^1$ is defined above, or $R^5$ and $R^6$, together with the carbon or nitrogen to which they are both attached, form a three to seven membered saturated ring containing from zero to three heterocarbons selected, independently, from O, N and S, and wherein said aryl, heteroaryl, and heterocyclic are defined as such terms are defined above in the definition of $R_1$, and wherein any of the aryl, heteroaryl and heterocyclic moieties of $R^2$ may optionally be substituted with from one to three substituents, independently selected from halo, $(C_1-C_6)$alkyl optionally substituted with from one to seven fluorine atoms, phenyl, benzyl, hydroxy, acetyl, amino, cyano, nitro, $(C_1-C_6)$alkoxy optionally substituted with from one to seven fluorine atoms, $(C_1-C_6)$alkylamino and $_2$amino;

$R^3$ is hydroxy, —$(C_1-C_6)$alkyl-OH, —$(C_1-C_6)$alkyl-$(C_1-C_6)$alkoxy, $NHSO_2R^7$, $C(OH)R^7R^8$, halo, or heteroaryl as defined for $R^1$ above or $CONHR^7$, wherein $R^7$ and $R^8$ are the same or different and are selected from hydrogen, $(C_1-C_4)$alkyl, $(C_1-C_4)$alkoxy and $(C_1-C_4)$alkoxy-$(C_1-C_4)$alkyl having in said $(C_1-C_4)$alkoxy-$(C_1-C_4)$alkyl a total of 4 or less carbon atoms, and wherein any of the alkyl moieties of $R^7$ and $R^8$ may optionally be substituted with from one to seven fluorine atoms; and $Z^1$ is hydrogen, halo or $(C_1-C_5)$alkyl;

with the proviso that there are no two adjacent ring oxygen atoms and no ring oxygen atom adjacent to either a ring nitrogen atom or a ring sulfur atom in any of the heterocyclic or heteroaryl moieties of formula I;

and the pharmaceutically acceptable salts of such compounds.

2. A compound according to claim 1 wherein n is zero or one;

$R^1$ is benzyl, cyclopropylmethyl, 2-pyridyl, 4-fluoro-2-pyridyl, pyrimidyl, 2-methylpentyl, 3-phenylpropyl, 2-ethoxyethyl or 3,5,5-trimethylhexyl; $R^2$ is CON(CH$_2$CH$_3$)$_2$, CON(CH$_3$)$_2$, CON(CH$_2$CH$_3$)CH$_3$, C(OH)(CH$_3$)$_2$, C(OH)(CH$_2$CH$_3$)$_2$, 3,3-dimethyloxazoline, 3,3-diethyloxazoline, benzoxazole, tetrazole or 3,5-dimethylpyrazole; and $R^3$ is OH, CONH$_2$, fluoro, bromo, chloro, iodo, or NHSO$_2R^7$.

3. A pharmaceutical composition for treating a disorder or condition selected from inflammatory diseases such as arthritis, psoriasis, asthma, or inflammatory bowel disease, disorders of respiratory function such as asthma, cough and apnea, allergies, gastrointestinal disorders such as gastritis, bowel disease, irritable bowel syndrome, diarrhea, distension, pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions, chronic pain, nonsomatic pain, acute pain and neurogenic pain, systemic lupus erythematosus, Hodgkin's disease, Sjogren's disease, epilepsy and rejection in organ transplants and skin grafts in a mammal, comprising an amount of a compound according to claim 1 that is effective in treating such disorder or condition and a pharmaceutically acceptable carrier.

4. A pharmaceutical composition for treating a disorder or condition, the treatment or prevention of which can be effected or facilitated by modulating binding to opioid receptors in a mammal, comprising an amount of a compound according to claim 1 that is effective in treating such disorder or condition and a pharmaceutically acceptable carrier.

5. A method for treating a disorder or condition selected from inflammatory diseases such as arthritis, psoriasis, asthma, or inflammatory bowel disease, disorders of respiratory function such as asthma, cough and apnea, allergies, gastrointestinal disorders such as gastritis, bowel disease, irritable bowel syndrome, diarrhea, distension, pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions, chronic pain, nonsomatic pain, acute pain and neurogenic pain, systemic lupus erythematosus, Hodgkin's disease, Siogren's disease, epilepsy and rejection in organ transplants and skin grafts in a mammal, comprising administering to a mammal requiring such treatment an amount of a compound according to claim 1 that is effective in treating such disorder or condition.

6. A method for treating a disorder or condition, the treatment of which can be effected or facilitated by modulating binding to opioid receptors in a mammal, comprising administering to a mammal requiring such treatment an amount of a compound according to claim 1 that is effective in treating such disorder or condition.

7. A pharmaceutical composition for treating a disorder or condition selected from inflammatory diseases such as arthritis, psoriasis, asthma, or inflammatory bowel disease, disorders of respiratory function such as asthma, cough and apnea, allergies, gastrointestinal disorders such as gastritis, bowel disease, irritable bowel syndrome, diarrhea, distension, pain, nonulcerogenic dyspepsia and other disorders of motility or secretion, and emesis, stroke, shock, brain edema, head trauma, spinal cord trauma, cerebral ischemia, cerebral deficits subsequent to cardiac bypass surgery and grafting, urogenital tract disorders such as urinary incontinence, chemical dependencies and addictions, chronic pain, nonsomatic pain, acute pain and neurogenic pain, systemic lupus erythematosus, Hodgkin's disease, Sjogren's disease, epilepsy and rejection in organ transplants and skin grafts in a mammal, comprising an opioid receptor binding modulating effective amount of a compound according to claim 1 and a pharmaceutically acceptable carrier.

8. A pharmaceutical composition for treating a disorder or condition, the treatment or prevention of which can be effected or facilitated by modulating binding to opioid receptors in a mammal, comprising an opioid receptor binding modulating effective amount of a compound according to claim 1 and a pharmaceutically acceptable carrier.

9. A compound selected from the group consisting of compounds of the formula

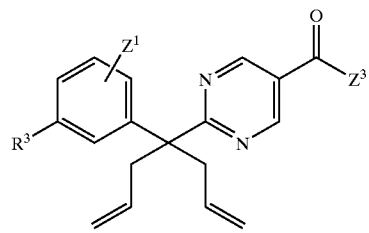

and

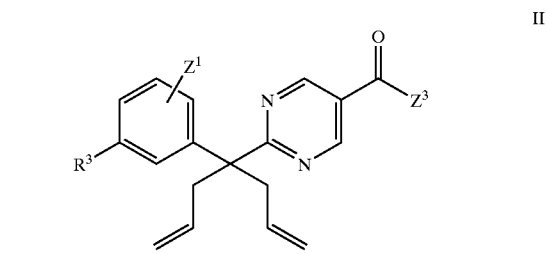

wherein $Z^3$ is hydrogen or $OR^{10}$ wherein $R^{10}$ is $(C_1-C_6)$alkyl, and wherein $Z^1$ is hydrogen, halo or $(C_1-C_5)$alkyl;

and $R^3$ is selected from hydroxy, —$(C_1-C_6)$alkyl-OH, —$(C_1-C_6)$alkyl-$(C_1-C_6)$alkoxy, NHSO$_2R^7$, C(OH)$R^7R^8$, halo, or heteroaryl wherein said heteroaryl is selected from pyrazinyl, benzofuranyl, quinolyl, isoquinolyl, benzothienyl, isobenzofuryl, pyrazolyl, indolyl, isoindolyl, benzimidazolyl, purinyl, carbazolyl, 1,2,5-thiadiazolyl, quinazolinyl, pyridazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, oxazolyl, oxadiazolyl, isoxazolyl, thiazolyl, isothiazolyl, furanyl, pyrrolyl, tetrazolyl, triazolyl, thienyl, imidazolyl, pyridinyl, and pyrimidinyl;

or CONHR$^7$, wherein R$^7$ and R$^8$ are the same or different and are selected from hydrogen, $(C_1-C_4)$alkyl, $(C_1-C_4)$alkoxy and $(C_1-C_4)$alkoxy-$(C_1-C_4)$alkyl having in said $(C_1-C_4)$alkoxy-$(C_1-C_4)$alkyl a total of 4 or less carbon atoms, and wherein any of the alkyl moieties of R$^7$ and R$^8$ may optionally be substituted with from one to seven fluorine atoms.

* * * * *